US009012403B2

(12) United States Patent
Petzelbauer et al.

(10) Patent No.: US 9,012,403 B2
(45) Date of Patent: Apr. 21, 2015

(54) PEPTIDES AS ACTIVE AGENTS TO STABILIZE BIOLOGICAL BARRIERS

(75) Inventors: Peter Petzelbauer, Vienna (AT); Sonja Reingruber, Perchtoldsdorf (AT)

(73) Assignee: XiberScience GmbH, Perchtoldsdorf (AT)

( * ) Notice: Subject to any disclaimer, the term of this patent is extended or adjusted under 35 U.S.C. 154(b) by 0 days.

(21) Appl. No.: 13/702,490

(22) PCT Filed: Jun. 17, 2011

(86) PCT No.: PCT/EP2011/060105
§ 371 (c)(1),
(2), (4) Date: Feb. 20, 2013

(87) PCT Pub. No.: WO2011/157819
PCT Pub. Date: Dec. 22, 2011

(65) Prior Publication Data
US 2013/0143791 A1 Jun. 6, 2013

(30) Foreign Application Priority Data
Jun. 18, 2010 (AT) .................................. A 1010/2010

(51) Int. Cl.
*A61K 38/00* (2006.01)
*C07K 7/06* (2006.01)
*C07K 7/08* (2006.01)
*C07K 14/705* (2006.01)

(52) U.S. Cl.
CPC . *C07K 7/06* (2013.01); *A61K 38/00* (2013.01); *C07K 7/08* (2013.01); *C07K 14/705* (2013.01)

(58) Field of Classification Search
CPC ............ A61K 38/00; C07K 7/06; C07K 7/08; C07K 14/705
USPC .................. 514/15.4, 1.5, 21.6; 530/327, 328
See application file for complete search history.

(56) References Cited

U.S. PATENT DOCUMENTS

| 3,773,919 | A | 11/1973 | Boswell et al. ............... 424/486 |
|---|---|---|---|
| 4,485,045 | A | 11/1984 | Regen .............................. 554/80 |
| 4,544,545 | A | 10/1985 | Ryan et al. .................... 424/1.21 |
| 4,711,955 | A | 12/1987 | Ward et al. ................. 536/25.32 |
| 5,525,711 | A | 6/1996 | Hawkins et al. .............. 536/22.1 |
| 5,792,608 | A | 8/1998 | Swaminathan et al. ...... 435/6.12 |
| 2004/0053250 | A1 | 3/2004 | Tang et al. ...................... 435/6.1 |

FOREIGN PATENT DOCUMENTS

| DE | 3218121 | 11/1983 |
|---|---|---|
| EP | 36676 | 9/1981 |
| EP | 52322 | 5/1982 |
| EP | 58481 | 8/1982 |
| EP | 88046 | 9/1983 |
| EP | 102324 | 3/1984 |
| EP | 133988 | 3/1985 |
| EP | 142641 | 5/1985 |
| EP | 143949 | 6/1985 |
| EP | 302175 | 2/1989 |
| WO | WO 2007/103515 | 9/2007 |
| WO | WO 2008/155134 | 12/2008 |

OTHER PUBLICATIONS

Acute Respiratory Distress Syndrome (ARDS) from Merck manual, pp. 1-2. Accessed Mar. 13, 2014.*
Acute Kidney Injury (AKI) from Merck manual, pp. 1-3. Accessed Mar. 13, 2014.*
Rudinger J, "Characteristics of the amino acids as components of a peptide hormone sequence," Peptide Hormones, JA Parsons Edition, University Park Press, Jun. 1976, pp. 1-7.*
"Designing Custom Peptides," from SIGMA Genosys, pp. 1-2. Accessed Dec. 16, 2004.*
Schinzel R, Drueckes P, "The phosphate recognition site of *Escherichia coli* maltodextrin phosphorylase," FEBS, Jul. 1991, 286(1,2): 125-128.*
Berendsen HJC, "A Glimpse of the Holy Grail?" Science, 1998, 282: 642-643.*
Voet D, Voet JG, Biochemistry, Second Edition, John Wiley & Sons, Inc., 1995, pp. 235-241.*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*
Water from www.biology-online.org/dictionary/Water, pp. 1-3. Accessed Apr. 24, 2014.*
Hopkins et al., "Modulation of tight junction function by G protein-coupled events", Adv. Drug Deliv Rev, 41:329-340, 2000.
Ivanov et al. "Cytoskeletal Regulation of Epithelial Barrier Function During Inflammation", Am. J. Pathol, 177(2):512-524, 2010.
Wu et al., "TNF induces caspase-dependent inflammation in renal endothelial cells through a Rho- and myosin light chain kinase-dependent mechanism", Am. J. Physiol Renal Physiol, 297(2):F316-F326, 2009.
Tinsley et al., "Myosin light chain phosphorylation and pulmonary endothelial cell hyperpermeability in burns", Am. J. Physiol. Lung Cell Mol. Physiol., 286:L841-L847, 2004.

(Continued)

*Primary Examiner* — Julie Ha
(74) *Attorney, Agent, or Firm* — Norton Rose Fulbright US LLP

(57) ABSTRACT

The present invention relates to compounds, in particular peptides which are capable of stabilizing barrier functions of epithelium and endothelium. The peptides and other compounds of the present invention are useful in the treatment and prevention of diseases or disorders associated with a localized or systemic breakdown of epithelial and endothelial barrier functions. Particular diseases and disorders to be treated and/or prevented with the peptides or other compounds, methods and uses provided herein are burns, acute lung injury (ALI), acute respiratory distress syndrome (ARDS), ventilator induced lung injury (VILI), systemic inflammatory response syndrome (SIRS), acute kidney injury (AKI), sepsis, multiorgan dysfunction syndrome (MODS), or edema.

14 Claims, 1 Drawing Sheet

(56) References Cited

OTHER PUBLICATIONS

Clements et al., "RhoA and Rho-kinase dependent and independent signals mediate TGF-beta-induced pulmonary endothelial cytoskeletal reorganization and permeability", Am. J. Physiol. Lung Cell Mol. Physiol., 288(2):L294-L306, 2005.
Birukova et al., "GEF-H1 is involved in agonist-induced human pulmonary endothelial barrier dysfunction", Am. J. Physiol. Lung Cell Mol. Physiol., 290(3):L540-L548, 2006.
Matute-Bello et al., "Animal models of acute lung injury", Am. J. Physiol. Lung Cell Mol. Physiol., 295(3):L379-399, 2008.
Birukova et al., "Mechanotransduction by GEF-H1 as a novel mechanism of ventilator-induced vascular endothelial permeability", Am. J. Physiol. Lung Cell Mol. Physiol., 298(6):L837-L848, 2010.
Matthay and Zimmerman, "Acute Lung Injury and the Acute Respiratory Distress Syndrome: Four Decades of Inquiry into Pathogenesis and Rational Management", Am. J. Resir. Cel. Mol. Biol., 33(4):319-327, 2005.
Carles et al., "Critical Role of the Small GTPase RhoA in the Development of Pulmaonary Edema Induced by Pseudomonas aeruginosa in Mice", Anesthesiology, 113:1134-1143, 2010.
Citi et al., "The Tight Junction Protein Cingulin Regulates Gene Expression and RhoA Signaling", Annals of the New York Academy of Science, 1123:134-145, 2008.
Randriamboavonjy et al., "The S1P2 receptor expressed in human platelets is linked to the RhoA-Rho kinase pathway and is down regulated in type 2 diabetes", Basic Res. Cardiol., 104:333-340, 2009.
Hall, Rho GTPases and the control of cell behaviour, Biochem Soc. Trans, 33:891-895, 2005.
Gorlatov and Medved, "Interaction of Fibrin(ogen) with the Endothelial Cell Receptor VE-Cadherin: Mapping of the Receptor-Binding Site in the NH2-Terminal Portions of the Fibrin beta Chains", Biochemistry, 41:4107-4116, 2002.
Zheng et al., "Role of Rho kinase and actin filament in the increased vascular permeability of skin venules in rats after scalding", Burns, 29(8):820-827, 2003.
Spindler et al., "Role fo GTPases in control of microvascular permeability", Cardiovasc. Res, 87(2):243-253, 2010.
Burridge and Wennerberg, "Rho and Rac Take Center Stage", Cell, 116:167-179, 2004.
Loirand et al., "Rho Kinases in Cardiovascular Physiology and Pathophysiology", Circ Res., 98(3):322-334, 2006.
Maniatis et al., "Inhaled activated protein C protects mice from ventilator-induced lung injury", Crit. Care, 14(2):R70, 14 pages, 2010.
O'Neal et al., "Prehospital statin and aspirin use and the prevalence of severe sepsis and acute lung injury/acute respiratory distress syndrome", Crit. Care Med., 39(6):1343-1350, 2011.
McHenry and Vargo-Gogola, "Pleiotropic Functions of Rho GTPase Signaling: a Trojan Horse or Achilles' Heel for Breast Cancer Treatment?", Curr. Drug Targets, 11(9):1043-1058, 2010.
Raghavendran et al., "Pharmacotherapy of Acute Lung Injury and Actue Respiratory Distress Syndrome", Curr. Med. Chem., 15(19):1911-1924, 2008.
Zhou and Liao, "Rho Kinase: An Important Mediator of Atherosclerosis and Vascular Disease", Curr. Pharm. Des., 15(27):3108-3115, 2009.
UniProt, "SubName: Full=Putative uncharacterized protein 0J1047_A06.104; SubName: Full=Putative uncharacterized protein P0475E07.130", Retrieved from EBI accession No. UNIPROT:Q8GRW2, Mar. 1, 2003.
UniProt, "SubName: Full=Putative uncharacterized protein", Retrieved from EBI accession No. UNIPROT:Q7X9P7, Oct. 1, 2003.
Aijaz et al., "Binding of GEF-H1 to the Tight Junction-Associated Adaptor Cingulin Results in Inhibition of Rho Signaling and G1/S Phase Transition", Dev. Cell, 8:777-786, 2005.
Birkenfeld et al., "GEF-H1 Modulates Localized RhoA Activation during Cytokinesis under the Control of Mitotic Kinases", Dev. Cell, 12:699-712, 2007.

Gosling, "Salt of the earth or a drop in the ocean? A pathophysiological approach to fluid resuscitation", Emer. Med. J., 20:306-315, 2003.
Carman, "The Endothelial Cytoskeleton", Endothelial Biomedicine, Cambridge Press, pp. 696-706, 2007.
Birukova et al., "p190RhoGAP mediates protective effects of oxidized phospholipids in the models of ventilator induced lung injury", Exp. Cell Res., 317(6):859-872, 2011.
Van Aelst and D'Souza-Schorey, "Rho GTPases and signaling networks", Genes Dev., 11:2295-2322, 1997.
Schmidt and Hall, "Guanine nucleotide exchange factors for Rho GTPases: turning on the switch", Genes Dev., 16:1587-1609, 2002.
Sahni et al., "The VE-cadherin binding domain of fibrinogen induces endothelial barrier permeability and enhances transendothelial migration of malignant breast epithelial cells", Int. J. Cancer, 125:577-584, 2009.
International Preliminary Report on Patentability issued in PCT Application No. PCT/EP2011/060105, mailed Jan. 3, 2013.
International Search Report and Written Opinion issued in PCT Application No. PCT/EP2011/060105, mailed Dec. 13, 2011.
Cioffi, "What's New in Burns and Metabolism", J Am. Coll. Surg., 192:241-254, 2001.
Saito et al., "Mechanisms of Signal Transduction: Deregulation and Mislocalization of the Cytokinesis Regulator ECT2 Activate the Rho Signaling Pathways Leading to Malignant Transformation", J. Biol. Chem., 279:7169-7179, 2004.
Chrzanowska-Wodnicka and Burridge, "Rho-stimulated Contractility Drives the Formation of Stress Fibers and Focal Adhesions", J Cell Biol., 133:1403-1415, 1996.
Meller et al., "CZH proteins : a new family of Rho-GEFs", J Cell. Sci., 118:4937-4946, 2005.
Pertz, "Spatio-temporal Rho GTPase signaling—where are we now?", J Cell. Sci., 123:1841-1850, 2010.
Imai et al., "Injurious Mechanical Ventilation and End-Organ Epithelial Cell Apoptosis and Organ Dysfunction in an Experimental Model of Acute Respiratory Distress Syndrome", Jama, 289(16):2104-2112, 2003.
Li et al., "Inhibition of Rho kinase by fasudil hydrochloride attenuates lung injury induced by intestinal ischemia and reperfusion", Life Sci., 88(1-2):104-109, 2011.
Li et al., "Fasudil attenuates lipopolysaccharide-induced acute lung injury in mice through the Rho/Rho kinase pathway", Med Sci Monit, 16(4):112-118, 2010.
Wang and Dudek, "Regulation of vascular permeability by sphingosine 1-phosphate", Microvasc Res., 77(1):39-45, 2009.
Samarin et al., "Rho/Rho-associated Kinase-II Signaling Mediates Disassembly of Epithelial Apical Junctions", Mol. Biol. Cell, 18:3429-3439, 2007.
Chang et al., "GEF-H1 Couples Nocodazole-induced Microtubule Disassembly to Cell Contractility via RhoA", Mol. Biol. Cell, 19(5):2147-2153, 2008.
Atasever et al., "Distinct Alterations in Sublignal Microcirculatory Blood Flow and Hemoglobin Oxygenation in On-Pump and Off-Pump Coronary Artery Bypass Graft Surgery", J. cardio. and Vas. Anesthesia, 25(5):784-790, 2011.
Ware and Matthay, "The Acute Respiratory distress Syndrome", N. Engl. J. Med., 342(18):1334-1349, 2000.
Herridge and Angus, "Acute Lung Injry—Affecting Many Lives", N. Engl. J. Med., 353(16):1736-1738, 2005.
Lee and Slutsky, "Sepsis and Endothelial Permeability", N. Engl. J. Med., 363:689-691, 2010.
Rossman et al., "GEF Means Go: Turning on Rho GTPases with Guanine Nucleotide-Exchange Factors", Nat. Rev. Mol. Cell Biol., 6(2):167-180, 2005.
Terry et al., "Spatially restricted activation of RhoA signaling at epithelial junctions by p114RhoGEF drives junction formation and morphogenesis", Nature Cell Biol., 13(2):159-166, 2011.
Imai et al., "Angiotensin-converting enzyme 2 protects from severe acute lung failure", Nature, 436:112-116, 2005.
Pertz et al., "Spatiotemporal dynamics of RhoA activity in migrating cells", Nature, 440(7087):1069-1072, 2006.

(56) References Cited

OTHER PUBLICATIONS

Citi et al., "The Tight Junction Protein Cingulin Regulates Gene Expression and RhoA Signaling", *NY Acad. Sci.*, 1165:88-98, 2009.
Terry et al., "Rho Signaling and Tight Junction Functions", *Physiology (Bethesda)*, 25(1):16-26, 2010.
Groger et al., "Peptide B[beta]15-42 Preserves Endothelial Barrier Function in Shock", *PloS ONE*, 4(4):e5391, 2009.
Reynoso et al., "A Role for Long Chain Myosinn Light chain Kinase (MLCK-210 in Microvascular Hyperpermeability During Severe Burns", *Shock*, 28:589-595, 2007.
Suzuki et al., "A postmarketing surveillance study of fasudil treatment after aneurysmal subarachnoid hemorrhage", *Surg. Neurol*, 68(2):126-132, 2007.
Beckers et al., "Driving Rho GTPase activity in endothelial cells regulates barrier integrity", *Thromb Haemost.*, 103(1):40-55, 2010.
Birukova et al., "Lung endothelial barrier protection by iloprost in the 2-hit models of ventilator-induced lung injury (VILI) involves inhibition of Rho signaling", *Transl. Res.*, 115(1):44-54, 2010.
Birkenfeld et al., "Cellular functions of GEF-H1, a microtubule-regulated Rho-GEF: is altered GEF-H1 activity a crucial determinant of disease pathogenesis?", *Trends Cell Biol.*, 18:210-219, 2008.

* cited by examiner

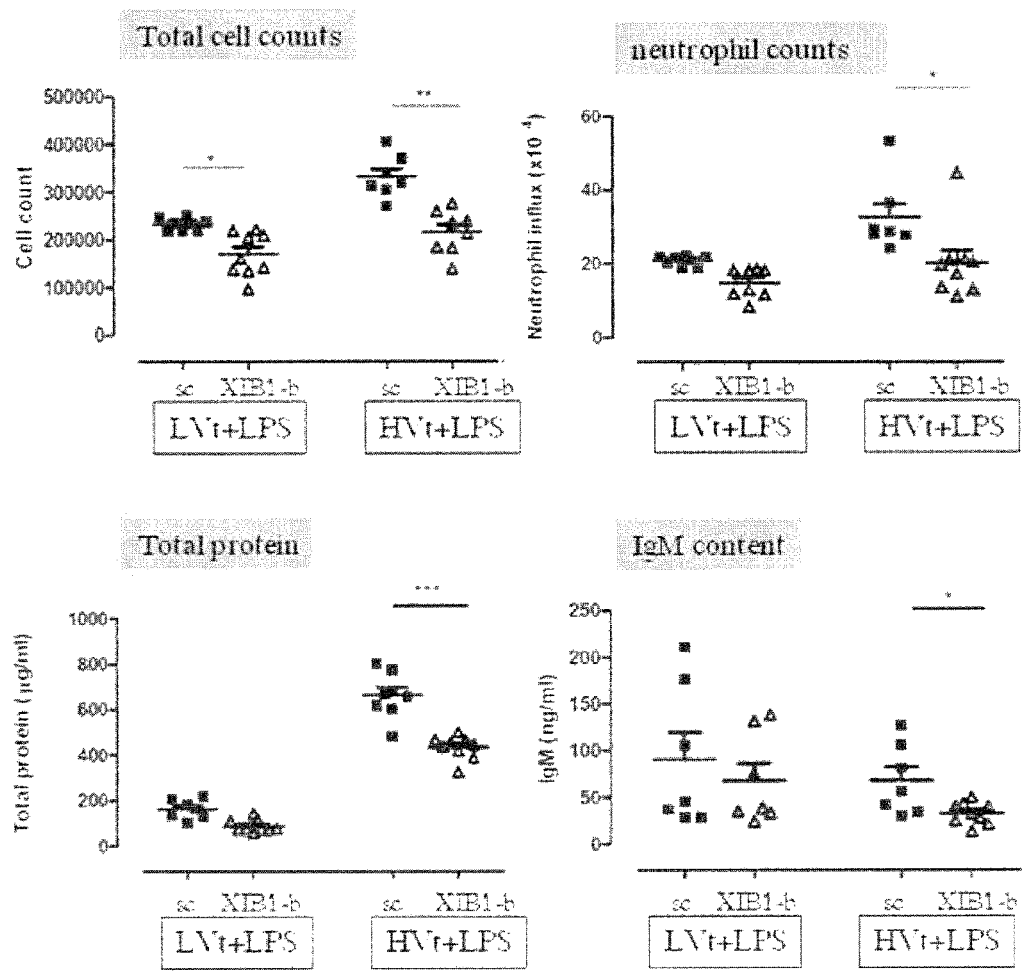

SEQUENCE LISTING

<160> NUMBER OF SEQ ID NOS: 41

<210> SEQ ID NO 1
<211> LENGTH: 11
<212> TYPE: PRT
<213> ORGANISM: artificial sequence
<220> FEATURE:
<221> NAME/KEY: source
<223> OTHER INFORMATION: /note="Description of artificial sequence:
      variable insert"
<220> FEATURE:
<221> NAME/KEY: misc_features
<222> LOCATION: (2)..(2)
<223> OTHER INFORMATION: Xaa is R or A
<220> FEATURE:
<221> NAME/KEY: misc_features
<222> LOCATION: (5)..(5)
<223> OTHER INFORMATION: Xaa is either omitted of L or V
<220> FEATURE:
<221> NAME/KEY: misc_features
<222> LOCATION: (6)..(6)
<223> OTHER INFORMATION: Xaa is either omitted or an amino acid sequence
      consisting of 1 to 5 amino acids
<220> FEATURE:
<221> NAME/KEY: misc_features
<222> LOCATION: (7)..(7)
<223> OTHER INFORMATION: Xaa is either omitted or GG
<220> FEATURE:
<221> NAME/KEY: misc_features
<222> LOCATION: (8)..(8)
<223> OTHER INFORMATION: Xaa is two amino acids selected from the group
      consisting of A, I and S
<220> FEATURE:
<221> NAME/KEY: misc_features
<222> LOCATION: (11)..(11)
<223> OTHER INFORMATION: Xaa is either omitted or an amino acid sequence
      consisting of 1 to 5 amino acids

<400> SEQUENCE: 1

Gly Xaa Arg Pro Xaa Xaa Xaa Xaa Gly Gly Xaa
1               5                   10

<210> SEQ ID NO 2
<211> LENGTH: 10
<212> TYPE: PRT
<213> ORGANISM: artificial sequence
<220> FEATURE:
<221> NAME/KEY: source
<223> OTHER INFORMATION: /note="Description of artificial sequence:
      cingulin-derived peptide"
<220> FEATURE:
<221> NAME/KEY: misc_feature
<222> LOCATION: (6)..(6)
<223> OTHER INFORMATION: Xaa is either omitted or GG

<400> SEQUENCE: 2

Gly Arg Arg Pro Leu Xaa Ile Ser Gly Gly
1               5                   10

<210> SEQ ID NO 3
<211> LENGTH: 11
<212> TYPE: PRT
<213> ORGANISM: artificial sequence
<220> FEATURE:
<221> NAME/KEY: source
<223> OTHER INFORMATION: /note="Description of artificial sequence:
      cingulin-derived peptide: XIB1-b"

<400> SEQUENCE: 3

Gly Arg Arg Pro Leu Gly Gly Ile Ser Gly Gly
1               5                   10

```
<210> SEQ ID NO 4
<211> LENGTH: 9
<212> TYPE: PRT
<213> ORGANISM: artificial sequence
<220> FEATURE:
<221> NAME/KEY: source
<223> OTHER INFORMATION: /note="Description of artificial sequence:
      cingulin-derived peptide"

<400> SEQUENCE: 4

Gly Arg Arg Pro Leu Ile Ser Gly Gly
1               5

<210> SEQ ID NO 5
<211> LENGTH: 10
<212> TYPE: PRT
<213> ORGANISM: artificial sequence
<220> FEATURE:
<221> NAME/KEY: source
<223> OTHER INFORMATION: /note="Description of artificial sequence:
      cingulin-derived peptide"
<220> FEATURE:
<221> NAME/KEY: misc_feature
<222> LOCATION: (6)..(6)
<223> OTHER INFORMATION: Xaa is either omitted or GG

<400> SEQUENCE: 5

Gly Arg Arg Pro Val Xaa Ile Ser Gly Gly
1               5                   10

<210> SEQ ID NO 6
<211> LENGTH: 11
<212> TYPE: PRT
<213> ORGANISM: artificial sequence
<220> FEATURE:
<221> NAME/KEY: source
<223> OTHER INFORMATION: /note="Description of artificial sequence:
      cingulin-derived peptide"

<400> SEQUENCE: 6

Gly Arg Arg Pro Val Gly Gly Ile Ser Gly Gly
1               5                   10

<210> SEQ ID NO 7
<211> LENGTH: 9
<212> TYPE: PRT
<213> ORGANISM: artificial sequence
<220> FEATURE:
<221> NAME/KEY: source
<223> OTHER INFORMATION: /note="Description of artificial sequence:
      cingulin-derived peptide"

<400> SEQUENCE: 7

Gly Arg Arg Pro Val Ile Ser Gly Gly
1               5

<210> SEQ ID NO 8
<211> LENGTH: 12
<212> TYPE: PRT
<213> ORGANISM: artificial sequence
<220> FEATURE:
<221> NAME/KEY: source
<223> OTHER INFORMATION: /note="Description of artificial sequence:
      cingulin-derived peptide"

<400> SEQUENCE: 8

Gly Arg Arg Pro Leu Pro Pro Pro Ile Ser Gly Gly
1               5                   10
```

```
<210> SEQ ID NO 9
<211> LENGTH: 12
<212> TYPE: PRT
<213> ORGANISM: artificial sequence
<220> FEATURE:
<221> NAME/KEY: source
<223> OTHER INFORMATION: /note="Description of artificial sequence:
      cingulin-derived peptide"

<400> SEQUENCE: 9

Gly Arg Arg Pro Val Pro Pro Pro Ile Ser Gly Gly
1               5                   10

<210> SEQ ID NO 10
<211> LENGTH: 11
<212> TYPE: PRT
<213> ORGANISM: artificial sequence
<220> FEATURE:
<221> NAME/KEY: source
<223> OTHER INFORMATION: /note="Description of artificial sequence:
      cingulin-derived peptide"

<400> SEQUENCE: 10

Gly Arg Arg Pro Leu Gly Gly Ala Ala Gly Gly
1               5                   10

<210> SEQ ID NO 11
<211> LENGTH: 11
<212> TYPE: PRT
<213> ORGANISM: artificial sequence
<220> FEATURE:
<221> NAME/KEY: source
<223> OTHER INFORMATION: /note="Description of artificial sequence:
      cingulin-derived peptide"

<400> SEQUENCE: 11

Gly Arg Arg Pro Val Gly Gly Ala Ala Gly Gly
1               5                   10

<210> SEQ ID NO 12
<211> LENGTH: 12
<212> TYPE: PRT
<213> ORGANISM: artificial sequence
<220> FEATURE:
<221> NAME/KEY: source
<223> OTHER INFORMATION: /note="Description of artificial sequence:
      cingulin-derived peptide"

<400> SEQUENCE: 12

Gly Arg Arg Pro Leu Pro Pro Pro Ala Ala Gly Gly
1               5                   10

<210> SEQ ID NO 13
<211> LENGTH: 12
<212> TYPE: PRT
<213> ORGANISM: artificial sequence
<220> FEATURE:
<221> NAME/KEY: source
<223> OTHER INFORMATION: /note="Description of artificial sequence:
      cingulin-derived peptide"

<400> SEQUENCE: 13

Gly Arg Arg Pro Val Pro Pro Pro Ala Ala Gly Gly
1               5                   10

<210> SEQ ID NO 14
<211> LENGTH: 11
<212> TYPE: PRT
<213> ORGANISM: artificial sequence
```

-continued

```
<220> FEATURE:
<221> NAME/KEY: source
<223> OTHER INFORMATION: /note="Description of artificial sequence:
      cingulin-derived peptide"

<400> SEQUENCE: 14

Gly Arg Arg Pro Leu Gly Gly Ala Ser Gly Gly
1               5                   10

<210> SEQ ID NO 15
<211> LENGTH: 11
<212> TYPE: PRT
<213> ORGANISM: artificial sequence
<220> FEATURE:
<221> NAME/KEY: source
<223> OTHER INFORMATION: /note="Description of artificial sequence:
      cingulin-derived peptide"

<400> SEQUENCE: 15

Gly Arg Arg Pro Val Gly Gly Ala Ser Gly Gly
1               5                   10

<210> SEQ ID NO 16
<211> LENGTH: 12
<212> TYPE: PRT
<213> ORGANISM: artificial sequence
<220> FEATURE:
<221> NAME/KEY: source
<223> OTHER INFORMATION: /note="Description of artificial sequence:
      cingulin-derived peptide"

<400> SEQUENCE: 16

Gly Arg Arg Pro Leu Pro Pro Pro Ala Ser Gly Gly
1               5                   10

<210> SEQ ID NO 17
<211> LENGTH: 12
<212> TYPE: PRT
<213> ORGANISM: artificial sequence
<220> FEATURE:
<221> NAME/KEY: source
<223> OTHER INFORMATION: /note="Description of artificial sequence:
      cingulin-derived peptide"

<400> SEQUENCE: 17

Gly Arg Arg Pro Val Pro Pro Pro Ala Ser Gly Gly
1               5                   10

<210> SEQ ID NO 18
<211> LENGTH: 11
<212> TYPE: PRT
<213> ORGANISM: artificial sequence
<220> FEATURE:
<221> NAME/KEY: source
<223> OTHER INFORMATION: /note="Description of artificial sequence:
      cingulin-derived peptide"

<400> SEQUENCE: 18

Gly Arg Arg Pro Leu Gly Gly Ile Ala Gly Gly
1               5                   10

<210> SEQ ID NO 19
<211> LENGTH: 11
<212> TYPE: PRT
<213> ORGANISM: artificial sequence
<220> FEATURE:
<221> NAME/KEY: source
<223> OTHER INFORMATION: /note="Description of artificial sequence:
      cingulin-derived peptide"
```

<400> SEQUENCE: 19

Gly Arg Arg Pro Val Gly Gly Ile Ala Gly Gly
1               5                   10

<210> SEQ ID NO 20
<211> LENGTH: 12
<212> TYPE: PRT
<213> ORGANISM: artificial sequence
<220> FEATURE:
<221> NAME/KEY: source
<223> OTHER INFORMATION: /note="Description of artificial sequence:
      cingulin-derived peptide"

<400> SEQUENCE: 20

Gly Arg Arg Pro Leu Pro Pro Pro Ile Ala Gly Gly
1               5                   10

<210> SEQ ID NO 21
<211> LENGTH: 12
<212> TYPE: PRT
<213> ORGANISM: artificial sequence
<220> FEATURE:
<221> NAME/KEY: source
<223> OTHER INFORMATION: /note="Description of artificial sequence:
      cingulin-derived peptide"

<400> SEQUENCE: 21

Gly Arg Arg Pro Val Pro Pro Pro Ile Ala Gly Gly
1               5                   10

<210> SEQ ID NO 22
<211> LENGTH: 11
<212> TYPE: PRT
<213> ORGANISM: artificial sequence
<220> FEATURE:
<221> NAME/KEY: source
<223> OTHER INFORMATION: /note="Description of artificial sequence:
      cingulin-derived peptide"

<400> SEQUENCE: 22

Gly Ala Arg Pro Leu Gly Gly Ile Ser Gly Gly
1               5                   10

<210> SEQ ID NO 23
<211> LENGTH: 11
<212> TYPE: PRT
<213> ORGANISM: artificial sequence
<220> FEATURE:
<221> NAME/KEY: source
<223> OTHER INFORMATION: /note="Description of artificial sequence:
      cingulin-derived peptide"

<400> SEQUENCE: 23

Gly Ala Arg Pro Val Gly Gly Ile Ser Gly Gly
1               5                   10

<210> SEQ ID NO 24
<211> LENGTH: 12
<212> TYPE: PRT
<213> ORGANISM: artificial sequence
<220> FEATURE:
<221> NAME/KEY: source
<223> OTHER INFORMATION: /note="Description of artificial sequence:
      cingulin-derived peptide"

<400> SEQUENCE: 24

Gly Ala Arg Pro Leu Pro Pro Pro Ile Ser Gly Gly

-continued

```
<210> SEQ ID NO 25
<211> LENGTH: 12
<212> TYPE: PRT
<213> ORGANISM: artificial sequence
<220> FEATURE:
<221> NAME/KEY: source
<223> OTHER INFORMATION: /note="Description of artificial sequence:
      cingulin-derived peptide"

<400> SEQUENCE: 25

Gly Ala Arg Pro Val Pro Pro Ile Ser Gly Gly
1               5                   10

<210> SEQ ID NO 26
<211> LENGTH: 11
<212> TYPE: PRT
<213> ORGANISM: artificial sequence
<220> FEATURE:
<221> NAME/KEY: source
<223> OTHER INFORMATION: /note="Description of artificial sequence:
      cingulin-derived peptide"

<400> SEQUENCE: 26

Gly Ala Arg Pro Leu Gly Gly Ala Ala Gly Gly
1               5                   10

<210> SEQ ID NO 27
<211> LENGTH: 11
<212> TYPE: PRT
<213> ORGANISM: artificial sequence
<220> FEATURE:
<221> NAME/KEY: source
<223> OTHER INFORMATION: /note="Description of artificial sequence:
      cingulin-derived peptide"

<400> SEQUENCE: 27

Gly Ala Arg Pro Val Gly Gly Ala Ala Gly Gly
1               5                   10

<210> SEQ ID NO 28
<211> LENGTH: 12
<212> TYPE: PRT
<213> ORGANISM: artificial sequence
<220> FEATURE:
<221> NAME/KEY: source
<223> OTHER INFORMATION: /note="Description of artificial sequence:
      cingulin-derived peptide"

<400> SEQUENCE: 28

Gly Ala Arg Pro Leu Pro Pro Ala Ala Gly Gly
1               5                   10

<210> SEQ ID NO 29
<211> LENGTH: 12
<212> TYPE: PRT
<213> ORGANISM: artificial sequence
<220> FEATURE:
<221> NAME/KEY: source
<223> OTHER INFORMATION: /note="Description of artificial sequence:
      cingulin-derived peptide"

<400> SEQUENCE: 29

Gly Ala Arg Pro Val Pro Pro Ala Ala Gly Gly
1               5                   10

<210> SEQ ID NO 30
```

```
<211> LENGTH: 11
<212> TYPE: PRT
<213> ORGANISM: artificial sequence
<220> FEATURE:
<221> NAME/KEY: source
<223> OTHER INFORMATION: /note="Description of artificial sequence:
      cingulin-derived peptide"

<400> SEQUENCE: 30

Gly Ala Arg Pro Leu Gly Gly Ala Ser Gly Gly
1               5                   10

<210> SEQ ID NO 31
<211> LENGTH: 11
<212> TYPE: PRT
<213> ORGANISM: artificial sequence
<220> FEATURE:
<221> NAME/KEY: source
<223> OTHER INFORMATION: /note="Description of artificial sequence:
      cingulin-derived peptide"

<400> SEQUENCE: 31

Gly Ala Arg Pro Val Gly Gly Ala Ser Gly Gly
1               5                   10

<210> SEQ ID NO 32
<211> LENGTH: 12
<212> TYPE: PRT
<213> ORGANISM: artificial sequence
<220> FEATURE:
<221> NAME/KEY: source
<223> OTHER INFORMATION: /note="Description of artificial sequence:
      cingulin-derived peptide"

<400> SEQUENCE: 32

Gly Ala Arg Pro Leu Pro Pro Pro Ala Ser Gly Gly
1               5                   10

<210> SEQ ID NO 33
<211> LENGTH: 12
<212> TYPE: PRT
<213> ORGANISM: artificial sequence
<220> FEATURE:
<221> NAME/KEY: source
<223> OTHER INFORMATION: /note="Description of artificial sequence:
      cingulin-derived peptide"

<400> SEQUENCE: 33

Gly Ala Arg Pro Val Pro Pro Pro Ala Ser Gly Gly
1               5                   10

<210> SEQ ID NO 34
<211> LENGTH: 11
<212> TYPE: PRT
<213> ORGANISM: artificial sequence
<220> FEATURE:
<221> NAME/KEY: source
<223> OTHER INFORMATION: /note="Description of artificial sequence:
      cingulin-derived peptide"

<400> SEQUENCE: 34

Gly Ala Arg Pro Leu Gly Gly Ile Ala Gly Gly
1               5                   10

<210> SEQ ID NO 35
<211> LENGTH: 11
<212> TYPE: PRT
<213> ORGANISM: artificial sequence
<220> FEATURE:
```

```
<221> NAME/KEY: source
<223> OTHER INFORMATION: /note="Description of artificial sequence:
      cingulin-derived peptide"

<400> SEQUENCE: 35

Gly Ala Arg Pro Val Gly Gly Ile Ala Gly Gly
1               5                   10

<210> SEQ ID NO 36
<211> LENGTH: 12
<212> TYPE: PRT
<213> ORGANISM: artificial sequence
<220> FEATURE:
<221> NAME/KEY: source
<223> OTHER INFORMATION: /note="Description of artificial sequence:
      cingulin-derived peptide"

<400> SEQUENCE: 36

Gly Ala Arg Pro Leu Pro Pro Pro Ile Ala Gly Gly
1               5                   10

<210> SEQ ID NO 37
<211> LENGTH: 12
<212> TYPE: PRT
<213> ORGANISM: artificial sequence
<220> FEATURE:
<221> NAME/KEY: source
<223> OTHER INFORMATION: /note="Description of artificial sequence:
      cingulin-derived peptide"

<400> SEQUENCE: 37

Gly Ala Arg Pro Val Pro Pro Pro Ile Ala Gly Gly
1               5                   10

<210> SEQ ID NO 38
<211> LENGTH: 11
<212> TYPE: PRT
<213> ORGANISM: artificial sequence
<220> FEATURE:
<221> NAME/KEY: source
<223> OTHER INFORMATION: /note="Description of artificial sequence:
      variable insert"

<400> SEQUENCE: 38

Gly Gly Gly Gly Gly Ser Arg Arg Ile Pro Leu
1               5                   10

<210> SEQ ID NO 39
<211> LENGTH: 10
<212> TYPE: PRT
<213> ORGANISM: artificial sequence
<220> FEATURE:
<221> NAME/KEY: source
<223> OTHER INFORMATION: /note="Description of artificial sequence:
      cingulin-derived peptide: XIB1-a"

<400> SEQUENCE: 39

Gly Arg Arg Pro Gly Gly Ala Ser Gly Gly
1               5                   10

<210> SEQ ID NO 40
<211> LENGTH: 11
<212> TYPE: PRT
<213> ORGANISM: artificial sequence
<220> FEATURE:
<221> NAME/KEY: source
<223> OTHER INFORMATION: /note="Description of artificial sequence:
      variable insert"
```

```
-continued

<400> SEQUENCE: 40

Gly Gly Gly Gly Gly Leu Ser Arg Arg Ile Pro
1               5                   10

<210> SEQ ID NO 41
<211> LENGTH: 29
<212> TYPE: PRT
<213> ORGANISM: artificial sequence
<220> FEATURE:
<221> NAME/KEY: source
<223> OTHER INFORMATION: /note="Description of artificial sequence:
      peptide Bbeta 15-42"

<400> SEQUENCE: 41

Gly His Arg Pro Leu Asp Lys Lys Lys Arg Glu Glu Ala Pro Ser Leu
1               5                   10                  15

Arg Pro Ala Pro Pro Pro Ile Ser Gly Gly Gly Tyr Arg
            20                  25
```

PEPTIDES AS ACTIVE AGENTS TO STABILIZE BIOLOGICAL BARRIERS

The present application is a national phase application under 35 U.S.C. §371 of International Application No. PCT/EP2011/060105 filed Jun. 17, 2011, which claims priority to Austrian Patent Application No. A1010/2010 filed Jun. 18, 2010, the entire text and figures of which disclosures are incorporated herein by reference without disclaimer.

Compounds, in particular peptides which are capable of stabilizing barrier functions of epithelium and endothelium, are described. The peptides and other compounds are useful in the treatment and prevention of diseases or disorders associated with a localized or systemic breakdown of epithelial and endothelial barrier functions. Particular diseases and disorders to be treated and/or prevented with the peptides or other compounds, methods and uses provided herein are burns, acute lung injury (ALI), acute respiratory distress syndrome (ARDS), ventilator induced lung injury (VILI), systemic inflammatory response syndrome (SIRS), acute kidney injury (AKI), sepsis, multiorgan dysfunction syndrome (MODS), or edema.

Rho GTPases control many aspects of cell behaviour such as the organization of the cytoskeleton, cell migration, cell cycle progression, cell proliferation, cell differentiation, gene expression, cell survival and apoptosis (Nature (2006), 440 (7087):1069-1072; Curr Drug Targets (2010), 11(9): 1043-1058). A main aspect in their function is the control of permeability of vascular (Cardiovasc Res (2010), 87(2): 243-253; Thromb Haemost (2010), 103(1): 40-55; Am J Physiol Lung Cell Mol Physiol (2005), 288(2): L294-L306) and epithelial surfaces (Am J Pathol (2010), 177(2): 512-524; Physiology (Bethesda) (2010), 25(1): 16-26). Because of their central role in regulating permeability, the activation of Rho GTPases is decisive for many pathophysiological processes associated with a break down in epithelial and endothelial barrier function. Such pathological processes may be disorders and diseases comprising burns, acute lung injury (ALI), acute respiratory distress syndrome (ARDS), ventilator induced lung injury (VILI), systemic inflammatory response syndrome (SIRS), acute kidney injury (AKI), sepsis, multiorgan dysfunction syndrome (MODS) (Med Sci Monit (2010), 16(4): 112-118; Microvasc Res (2009), 77(1): 39-45; Anesthesiology (2010), 113:1134-1143; Curr Pharm Des (2009), 15(27): 3108-3115; Mol interventions (2004), 4(6): 349-357; Circ Res (2006), 98(3): 322-334; Am J Physiol Renal Physiol (2009), 297(2): F316-F326; Exp Cell Res (2011), 317(6): 859-872; Transl Res (2010), 155(1): 44-54; Burns (2003), 29(8): 820-827) or edema, particularly diseases associated with progressive tissue edema (N Engl J Med (2010), 363: 689-691). For treatment of these diseases, pharmacological inhibition of Rho GTPases and subsequent Rho-kinases is a promising approach (Trends Cell Biol (2008), 18: 210-219). Statins and bisphosphonates are substances which affect biosynthesis of isoprenoids and, thus, prevent lipid modification of Rho GTPases which are necessary for their activation as described below. Statins and bisphosphonates are tested in clinical studies as pharmaceuticals against cancer and cardiac diseases as well as for their capability to improve disturbed vascular and epithelial barrier function. For example, Fasudil is a Rho-kinase inhibitor which is used in vasospasms of brain arteries and lung hypertension. Furthermore, a VE-cadherin binding, fibrin-derived protein, Bβ15-42, has been described to stabilize endothelial barriers via inhibition of the Rho GTPase RhoA (PloS ONE (2009), 4(4): e5391).

Because of their central role in cell biology, the activity of Rho GTPases is strictly controlled. Rho GTPases cycle between an inactive, GDP-bound, state and an active GTP-bound state. Rho GTPases can interact with their effector molecules and affect their functions only in the GTP-bound form. Most GTPases in active form are bound to the cell membrane. This membrane-targeting is mediated by C-terminal polybasis region and a post-translational isoprenylation of the Rho GTPases. The active exists only for a limited time as due to the hydrolyse-activity of Rho GTPases, the bound GTP is quickly converted to GDP. The GDP-bound state is more stable, therefore the major part of cellular RhoGTPases is inactive. So-called guanidine dissociation inhibitors (GDIs) mask the membrane-targeting sequences of the Rho GTPases and stabilize the GDP-bound conformation. The activation of RhoGTPases is mediated by specific guanine-nucleotide-exchange factors (GEFs), which catalyze the exchange of GDP for GTP; see also herein below. GEFs enhance the rate of dissociation of GDP and stabilize the nucleotide-free form of Rho GTPases. Since GTP is present in the cell in high molecular excess, the binding of GTP is favored. GTP-binding evokes a conformational change of the Rho GTPase such that the GEFs dissociate. The balance between active and inactive RHO GTPAses is further regulated by a another group of regulatory proteins, the GTPase-activating proteins (GAPs). GAPs increase the intrinsic Rho GTPAse hydrolyse activity of the Rho GTPases and, thus, favour their inactivation (Trend Cell Biol (2008), 18: 210-219). In their active form, Rho GTPases interact with high affinity with one of several downstream effectors. The active state is very transient; it is terminated by hydrolysis of GTP to GDP, a reaction that is stimulated by GAPs. In addition, guanine nucleotide dissociation factors stabilize the inactive form of Rho GTPases (Genes Dev. 1997; 11: 2295-2322; Biochem Soc Trans (2005); 33: 891-895; Cell (2004); 116: 167-179).

One possibility to control context-specific Rho GTPase activity is via guanine-nucleotide-exchange factors (GEFs). GEFs are upstream regulators of RhoGTPase activity. GEFs control Rho GTPase activity in a spatio-temporal- and partially context-specific manner (Nature Cell Biol (2011), 13: 159-166). In other words, GEFs allow activation of Rho in a defined time and location within a given cell. They integrate and process multiple outer signals and are themselves strictly controlled. They act like interfaces linking incoming signals to certain Rho GTPase driven cell biologic responses (Trends Cell Biol 2008; 18:210-19). The regulatory features of GEFs are due to their multi-domain architecture. The first Rho GEF was isolated from lymphoma cells as transformed gene and was named Dbl (Nat Rev Mol Cell Biol (2005), 6(2): 167-180). Meanwhile, the Dbl homology family comprises over 70 proteins. Most GEFs contain a highly conserved homology domain of about 200 amino acids which mediates the exchange of GDP and GTP in Rho GTPases. This domain is designated the DH-domain. The specificity of GEFs for a single or group of GTPases is conferred by this DH domain. The N-terminal domain is autoinhibitory, i.e. in the inactive state the N-terminus is phosphorylated and interacts with the DR-domain. Upon dephosphorylation, the auto-inhibition is resolved (Trend Cell Biol (2008), 18: 210-219; Protein Sci (2011), 20: 107-111). Additionally, there is a second subfamily of GEFs comprising 11 members which do not carry a DH domain. Instead of a DH domain, they contain two homology regions, namely DHR1 and DHR2 (dock homology region 1 and 2) (Trends Cell Biol (2008), 18: 210-219; J Cell Sci (2005), 118: 4937-4946; Nat Rev Mol Cell Biol (2005), 6(2): 167-180). GEFs bind the Rho GTPases via their homology domain(s) and, thus, assist exchange of GDP with GTP.

GEFs comprise a Pleckstrin-Domain (PH-Domain) close to the DH domain. The PH domain is involved in catalytic activity and mediation of protein-protein interaction. Together, the DH and the PH domain provide the minimal structure that is required for GTPase activation. The PH-domain is involved in the subcellular distribution of GEFs and in regulating activity (Genes Dev (2002), 16: 1587-1609; Nat Rev Mol Cell Biol (2005), 6(2): 167-180). For example, GEF-H1 is inactive when it is associated with microtubuli and tight junctions. In the active state, GEF-H1 relocates into the cytoplasm (Mol Biol Cell (2008), 19(5): 2147-2153; Dev Cell (2005), 8: 777-786).

GEF activity is controlled by intramolecular inhibition. The N-terminal domain of the GEFs functions as auto-inhibitor wherein intramolecular interaction is neutralized by phosphorylation. Thus, the target-GTPase can interact with the DH domain. Targeting of Rho GEFs at specific subcellular regions is also an important control mechanism of GEF activity. For example, inactive GEF-H1 is associated with microtubuli where it is bound to the inner membrane. In an active state, GEF-H1 dissociates and re-localizes in the cytoplasm (Trends in Cell Biol (2008), 18: 210-219).

GEF/RhoGTPases pathways regulate a number of central cell biologic processes such as organization of the cytoskeleton, gene expression, cell cycle progression and cell differentiation as well as apoptotic and non-apoptotic processes and cell motility, antigen presentation, epithelial and endothelial permeability (Cardiovasc Res (2010), 87(2): 243-253; Thromb Haemost (2010), 103(1): 40-55; Am J Physiol Lung Cell Mol Physiol (2005), 288(2): L294-L306; Am J Pathol (2010), 177(2): 512-524; Physiology (Bethesda) (2010), 25(1): 16-26). Due to its central role in cell physiology, the dysregulation of GEF/RhoGTPase pathways is a major component of pathophysiologic signal transduction in inflammatory diseases, endothelial and epithelial barrier dysfunction and cancer.

The GEF-H1/RhoA-pathway activates the cellular contractile apparatus consisting of actin and myosin and is required for junction dissociation (Mol Biol Cell (2007), 18: 3429-3439). Conversely, the p114RhoGEF induced RhoA activation is required for tight junction assembly (Nat Cell Biol (2011), 13(2): 159-166). A site and context-specific regulation of RhoA is decisive for maintenance of physiological barriers such as epithelial and endothelial layers. Endothelial and epithelial cells form continuous layers lining the inner lumen of blood vessels or the visceral cavities respectively. They form semi-permeable barriers and regulate the exchange of fluid and nutrients of neighboring tissues. A balanced RhoA activity is curial for physiologic epithelial and endothelial barrier function. Quiescent endothelial and epithelial cells show a basal RhoA activity, actin fibers and myosin bundles are restricted to the cell boarders to stabilize the tissue (Endothelial Biomedicine, Cambridge Press (2007), 696-706; J Cell Biol (1996), 133: 1403-1415). Stimulation with pro-inflammatory or pro-thrombotic agents results in activation of the GEF/RhoA pathway that in turn induces cyto-skeletal activation (J Cell Biol (1996), 133: 1403-1415). Actin and myosin form contractile bundles that pervade the cells as a result the cells constrict, neighboring cells loosen their contact. Opening of the cell-cell boarder is an important physiologic process e.g., in tissue proliferation and inflammatory processes to facilitate migration of inflammatory cells. But aberrant GEF/RhoA over-activation results in the breakdown of epithelial and/or endothelial barriers and is a major contributor to the pathophysiology of many serious diseases. (Adv Drug Deliv Rev (2000), 41: 329-40; Ann NY Acad Sci (2008), 1123: 134-45; Trends Cell Biol (2008), 18: 210-219) For example, GEF-H1 inhibition prevents acute lung injury (ALI) caused by mechanical ventilation in a mouse model (Am J Physiol Lung Cell Mol Physiol (2010), 298(6): L837-L848).

Acute lung injury (ALI) is a serious condition defined by bilateral lung infiltrates and hypoxia (N Engl J Med (2005), 353(16): 1736-8; Am J Resp Crit Care Med (1994), 149: 818-824). Acute respiratory distress syndrome (ARDS) is a severe form of ALI. With an incidence rate of 79 per 100.000 and a mortality of 40%, ALI is a major problem in intense care units (ICU). ALI is either induced by impact on the lung (such as pneumonia, acid aspiration, smoke inhalation, mechanical ventilation) or develops as a sequel of sepsis and trauma. Even though ALI develops from different ethiologies, all patient show common symptoms such as protein-rich edema and infiltration of inflammatory cells in the lung (N Engl J Med (2000); 34208): 1334-1349; Am J Respir Cel Mol Biol (2005), 33(4): 319-327). A LPS inhalation model in rodents is widely used in the search for therapeutical intervention possibilities in ALI. LPS inhalation induces a protein-rich edema and cellular inflammation due to a breakdown of endothelial and epithelial barriers (Am J Physiol Lung Cell Mol Physiol (2008), 295(3): L379-L399; Jama (2003), 289(16): 2104-2112; Nature (2005), 436: 112-116). GEF-H1 inhibition reduces the lung damage in a mouse model of ventilator induced lung injury (VILI) (Am J Physiol Lung Cell Mol Physiol (2010), 298(6): L837-L848) and improves endothelial barrier dysfunction (Am J Physiol Lung Cell Mol Physiol (2006), 290(3): L540-L548).

Major cutaneous burns (thermal & chemical) striking more than 15% of the total body surface area result not only in localized tissue damage but also in broad systemic inflammations such as systemic inflammatory response syndrome (SIRS) causing organ system damage distal to the burn site. SIRS also includes oedema, microvascular hyperpermeability, hypovolemic shock and multiple organ failure (multiple organ dysfunction syndrome) and ARDS (J Am Coll Surg (2001), 192: 241-254). One of the most damaging effects of burn injuries is the systemic inflammation that peaks within the first 3 h after the incidence and declines over the following 24-48 h (Clin Plast Surg (2000), 27: 11-22; World J Surg (1992), 16: 2-9).

The number of studies investigating the role of GEF/RhoA pathways in the pathophysiology of disorders such as major burns is very limited. But there are studies that suggest a contribution of myosin light chain kinase (MLCK) and Rho kinase to the development of SIRS and capillary leak after burns. Both molecules, MLCK and Rho kinase, are downstream effectors of RhoA. It is shown that endothelial cells loose their barrier function upon re-incubation with plasma isolated from burned rats. The endothelial hyperpermeability can be reverted by treating the endothelial cells with a MLCK inhibitor (AM J Physiol Lung Cell Mol Physiol (2004), 286: L841-L847). Pharmacologic inhibition of MLCK after scald injury improves outcome in vivo (Shock (2003), 20: 363-368). A knockout of MLCK-210 in mice reduces capillary leak and improves survival in a mouse model of burns (Shock (2007), 28: 589-595). Inhibition of Rho kinase decreases the vascular leak after scald injury in vivo (Burns (2003), 29(8): 820-827).

Accordingly, decreasing Rho GTPase activity may be a useful strategy in treating disorders and diseases associated with high activity of Rho GTPases. When aiming at inhibiting GEF function for decreasing Rho GTPases, the main issue is to achieve specificity in time and location and to target protein-protein interaction sites. However, the complex nature of these interaction sites is still not completely understood. In fact, known Rho GTPase- and Rho-kinase-inhibitors act systemically, i.e. they influence Rho-GTPases and Rho-kinases also in healthy cells/tissue and, thus, may imply severe side effects such as toxic myopathy (for statins) and may cause hypotension (Fasudil) (Surg Neurol (2007), 68(2): 126-131). Moreover, statins have to be supplied as a prophylactic treatment, i.e. prehospital treatment is required (Crit Care Med (2011), 39(6): 1343-1350.). This also applies for Fasudil where pretreatment was required in animal models (Life Sci (2011), 88(1-2): 104-109).

Therefore, there is a need for specific Rho GTPase inhibitors.

This technical problem has been solved by the embodiments provided herein and as provided in the appended examples and in the claims.

The present invention describes and provides peptides comprising or consisting of the amino acid sequence $$GX_1RPX_2X_3X_4X_5GGX_6 \quad (SEQ\ ID\ NO: 1)$$

wherein
$X_1$ is an amino acid selected from the group consisting of R and A;
$X_2$ is either omitted or an amino acid selected from the group consisting of L and V;
$X_3$ is either omitted or an amino acid sequence consisting of 1 to 5 amino acids;
$X_4$ is either omitted or an amino acid sequence consisting of GG;
$X_5$ represents two amino acids selected from the group consisting of A, I and S; and
$X_6$ is either omitted or an amino acid sequence consisting of 1 to 5 amino acids.

In certain circumstances, $X_6$ may also comprise or consist of more than 5 amino acids as described herein below.

The peptides of the present invention preferably comprise or consist of not more than 19 amino acid, more preferably not more than 14 amino acids, most preferably not more than 11 amino acids or not more than 9 amino acids. In one embodiment, the peptide of the present invention comprises or consists of 11 amino acids.

As used herein, the term "amino acid" refers to any amino acid known in the art and comprises proteinogenic as well as non-proteinogenic amino acids as known in the art. Proteinogenic amino acids comprise alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophane (Trp; W), tyrosine (Tyr; Y), valine (Val; V), selenocysteine (Sec; U) and pyrrolysine (Pyl; O). Non-limiting examples for non-proteinogenic amino acids are hydroxyproline, selenomethionine, carnitine, gamma-aminobutyric acid (GABA), lanthionine, dehydroalanine, ornitine, or citrulline. As the skilled person is readily aware of it is possible that in some cases also non-proteinogenic amino acids may be part of proteins. Amino acids are abbreviated herein by the one-letter code or the three-letter code as commonly used in the art and as also set forth hereinabove.

As has been surprisingly found in context of the present invention, the peptides described and provided herein are capable of inhibiting GTPases. This has been exemplarily demonstrated in the appended examples for RhoA. Particularly, as described and exemplified herein, these inventive peptides are useful in treating or preventing diseases or disorders caused by an aberrant activation of Rho GTPases. Such diseases and disorders comprise inter alia inflammatory diseases that are related to a loss of endothelial and/or epithelial barrier function. For example, the peptides of the present invention were shown to reduce lung inflammation which correlates with less lung damage and reduces pulmonary edema; cf. FIG. 1. The breakdown of endothelial and/or epithelial barriers is a major component of the pathophysiology of diseases or disorders associated with a localized or systemic breakdown of epithelial or endothelial barrier functions. Diseases or disorders which are treatable or preventable by the inventive means and methods comprise particularly burns, acute lung injury (ALI), acute respiratory distress syndrome (ARDS), ventilator induced lung injury (VILI), systemic inflammatory response syndrome (SIRS), acute kidney injury (AKI), sepsis, multiorgan dysfunction syndrome (MODS) or edema. As already mentioned, in accordance with the present invention, SIRS also comprises edema, microvascular hyperpermeability, and hypovolemic shock. In context with the present invention, edema which are treatable and/or preventable by the means and method as provided herein may particularly be diseases associated with progressive tissue edema as known in the art and as described, e.g., in N Engl J Med (2010), 363: 689-691. The peptides provided herein act through their capability to stabilize endothelial and epithelial barriers, reducing edema formation and inflammation, thereby improving organ function. Accordingly, the means and methods described and provided herein are particularly useful in treating and/or preventing diseases or disorders associated with a localized or systemic breakdown of epithelial or endothelial barrier functions. In particular, the peptides and methods of the present invention are useful in treating and/or preventing burns, acute lung injury (ALI), acute respiratory distress syndrome (ARDS), ventilator induced lung injury (VILI), systemic inflammatory response syndrome (SIRS), acute kidney injury (AKI), sepsis, multiorgan dysfunction syndrome (MODS) or edema.

The peptides described and provided in the present invention are derived from cingulin, a known GEF-H1 inhibitor (NY Acad Sci (2009), 1165: 88-98; Dev Cell (2005), 8: 777-786; Dev Cell (2007), 12: 699-712).

Furthermore, the peptides described and provided herein show sequence similarity with the VE-cadherin binding and RhoA-inhibiting protein Bβ15-42 (PLoS ONE (2009), 4(4): e5391). The activity of Bβ15-42 has repeatedly been described as being strongly dependent on the first four amino acids (Int J Cancer (2009), 125: 577-584). Particularly $His_{16}$ ($2^{nd}$ position of Bβ15-42) and $Arg_{17}$ ($3^{rd}$ position of Bβ15-42) of Bβ15-42 have been described as being critical (Biochemistry (2002), 41: 4107-4116) for functionality of Bβ15-42. In contrast thereto, the peptides described and provided in the present invention do not have a His at the $2^{nd}$ position but are nevertheless shown to have strong RhoA-inhibitory effects. Also, the herein described peptides target endothelial as well as epithelial cells, the latter lacking VE-cadherin. Moreover, it has surprisingly been found in the present invention that peptides described and provided herein are significantly more effective than Bβ15-42 as exemplarily demonstrated using an animal model for ALI (see, e.g., Example 6).

The peptides described and provided herein may further comprise $X_7$ at the C-terminus, wherein $X_7$ is a moiety which is suitable to delay primary renal filtration, to prolong serum half life and/or to protect against proteolytic degradation (particularly peptidases) of the peptides provided herein. Such moieties are known in the art. Non-limiting examples for such moieties are $NH_2$, albumin, polyethyleneglycol, dextrane, ferritine, hydroxyethyl-starch and the Fc-moiety of an antibody. $X_7$ may also be or comprise an amino acid stretch that is capable of prolonging serum half-life as described in, e.g., WO 08/155,134 or amino acid sequences as described in WO 07/103,515 or in Nat Biotechnol (2009), 27: 1186-1190.

In the following, non-limiting examples for variables $X_1$ to $X_6$ of the general sequence of the peptides described and provided herein are described. The peptides of the present invention may comprise one of the following specific examples of the variables or a combination of two, three or more thereof. $X_1$ is for example an R. $X_2$ may be an L or a V, for example an L. $X_3$ may be omitted or PPP, for example omitted. $X_4$ may be GG. $X_5$ may be IS or AS, for example IS. $X_6$ may be omitted or may be an additional amino acid or amino acid stretch. Said 1 to 5 amino acids of $X_6$ may be selected from any amino acid as described herein. Furthermore, in certain circumstances, $X_6$ may comprise or consist of more than 5 amino acids. It is also envisaged that $X_6$ may comprise a longer amino acid stretch, even an amino acid stretch larger than 15 amino acids. Such a stretch may also comprise an amino acid stretch that prolongs serum half-life as described for $X_7$ above, like the "PAS" sequences provided in WO 08/155,134, or the peptide sequences provided in WO 07/103,515 or in Nat Biotechnol (2009), 27: 1186-1190. However $X_6$ may also be omitted. In one embodiment, the peptide of the present invention comprises or consists of the amino acid sequence GRRPLX$_4$ISGG (SEQ ID NO: 2), e.g., GRRPLGGISGG (SEQ ID NO: 3) or GRRPLISGG (SEQ ID NO: 4). In another embodiment, the peptide of the present invention comprises or consists of the amino acid sequence GRRPVX$_4$ISGG (SEQ ID NO: 5), e.g., GRRPVGGISGG (SEQ ID NO: 6) or GRRPVISGG (SEQ ID NO: 7). In a particular embodiment, the peptide of the present invention comprises or consists of the amino acid sequence GRRPLGISGG (SEQ ID NO: 3).

The present invention relates to the following non-limiting specific examples for the peptides described and provided herein. In particular, the inventive peptides may comprise or consist of any one of the following sequences:

```
GRRPLGGISGG;          (SEQ ID NO: 3)

GRRPVGGISGG;          (SEQ ID NO: 6)

GRRPLISGG;            (SEQ ID NO: 4)

GRRPVISGG;            (SEQ ID NO: 7)

GRRPLPPPISGG;         (SEQ ID NO: 8)

GRRPVPPPISGG;         (SEQ ID NO: 9)

GRRPLGGAAGG;          (SEQ ID NO: 10)

GRRPVGGAAGG;          (SEQ ID NO: 11)

GRRPLPPPAAGG;         (SEQ ID NO: 12)

GRRPVPPPAAGG;         (SEQ ID NO: 13)

GRRPLGGASGG;          (SEQ ID NO: 14)
```

```
GRRPVGGASGG;          (SEQ ID NO: 15)

GRRPLPPPASGG;         (SEQ ID NO: 16)

GRRPVPPPASGG;         (SEQ ID NO: 17)

GRRPLGGIAGG;          (SEQ ID NO: 18)

GRRPVGGIAGG;          (SEQ ID NO: 19)

GRRPLPPPIAGG;         (SEQ ID NO: 20)

GRRPVPPPIAGG;         (SEQ ID NO: 21)

GARPLGGISGG;          (SEQ ID NO: 22)

GARPVGGISGG;          (SEQ ID NO: 23)

GARPLPPPISGG;         (SEQ ID NO: 24)

GARPVPPPISGG;         (SEQ ID NO: 25)

GARPLGGAAGG;          (SEQ ID NO: 26)

GARPVGGAAGG;          (SEQ ID NO: 27)

GARPLPPPAAGG;         (SEQ ID NO: 28)

GARPVPPPAAGG;         (SEQ ID NO: 29)

GARPLGGASGG;          (SEQ ID NO: 30)

GARPVGGASGG;          (SEQ ID NO: 31)

GARPLPPPASGG;         (SEQ ID NO: 32)

GARPVPPPASGG;         (SEQ ID NO: 33)

GARPLGGIAGG;          (SEQ ID NO: 34)

GARPVGGIAGG;          (SEQ ID NO: 35)

GARPLPPPIAGG;         (SEQ ID NO: 36)
or

GARPVPPPIAGG.         (SEQ ID NO: 37)
```

As already mentioned, in accordance with the present invention, a peptide comprising or consisting of any one of the above particular sequences may further comprise a moiety $X_7$ at the C-terminus as defined herein.

Methods for synthesizing peptides are know in the art and comprise, e.g., standard FMOC-synthesis as described in the literature (e.g., solid phase peptide synthesis—"A practical approach" by E. Atherton, R. C. Sheppard, Oxford University press 1989) or liquid phase synthesis, where the peptides are assembled using a mixed strategy by BOC-chemistry and fragment condensation as described in the literature (E. Wünsch, "Synthese von Peptiden" in "Methoden der organischen Chemie" (Houben-Weyl), 15 Ausg. 4, Teil 1 und 2 Thieme, Stuttgart, 1974).

The peptides described and provided herein may be capable of inhibiting activity of a Rho GTPase, e.g., RhoA. Methods for assessing Rho GTPase activity are known in the art and as described and exemplified herein. Non-limiting examples for methods suitable for assessing Rho GTPase activity include determination of global Rho GTPase activity as described in J Biol Chem (2004), 279: 7169-7179. Such an assay may be performed by using Rho substrates (e.g., Rhotekin) tagged with GST which are mixed into cell lysates, followed by a pull down using anti-GST antibodies. Detection may be carried by gel electrophoresis and Western blot using anti-Rho antibodies as known in the art. Another suitable method assessing Rho GTPase activity is a G-LISA assay as described in Basic Res Cardiol (2009), 104: 333-340. Still another way to assess Rho GTPase activity may be the determination of site spatio-temporal Rho activation within a given cell by using Rho GTPase activation biosensors such as GFP-effector sensors or unimolecular or bimolecular FRET sensors transfected or recombinantly expressed in a given cell. These biosensors allow spatio-temporal in vivo imaging of individual active Rho GTPases (J Cell Science (2010), 123: 1841-1850). Also, commercial kits for assessing RhoGTPase activity are available such as, e.g., "RhoGEF Exchange Assay Biochem Kit" from Cytoskeleton, Inc. For example, a given peptide may be considered a peptide of the present invention (1) if it comprises or consists of a sequence as defined herein, and (2) if it decreases Rho GTPase (e.g., RhoA) activity of a test cell at least 1.5-fold, at least 2-fold, at least 2.5-fold or at least 3-fold compared to the respective Rho GTPase activity (e.g., RhoA) of a reference cell (belonging to the same cell line) not treated with the peptide.

The present invention also relates to polynucleotides encoding the peptides described and provided herein. These polynucleotides may be nucleic acid analogues such as, e.g., DNA molecules, RNA molecules, oligonucleotide thiophosphates, substituted ribo-oligonucleotides, LNA molecules, PNA molecules, GNA (glycol nucleic acid) molecules, TNA (threose nucleic acid) molecules, or morpholino polynucleotides. Furthermore, the term "polynucleotide" is to be construed equivalently with the term "nucleic acid molecule" in context with the present invention and may inter cilia refer to DNA, RNA, PNA or LNA or hybrids thereof or any modification thereof that is known in the art (see, e.g., U.S. Pat. No. 5,525,711, U.S. Pat. No. 4,711,955, U.S. Pat. No. 5,792,608 or EP 302175 for examples of modifications). Nucleic acid residues comprised by the polynucleotides described and provided herein may be naturally occurring nucleic acid residues or artificially produced nucleic acid residues. Examples for nucleic acid residues are adenine (A), guanine (G), cytosine (C), thymine (T), uracil (U), xanthine (X), and hypoxanthine (HX). As understood by the person of skill in the art, thymine (T) and uracil (U) may be used interchangeably depending on the respective type of polynucleotide. For example, as the skilled person is aware of, a thymine (T) as part of a DNA corresponds to an uracil (U) as part of the corresponding transcribed mRNA. The polynucleotides described and provided herein may be single- or double-stranded, linear or circular, natural or synthetic.

Furthermore, in accordance with the present invention, the polynucleotides described in and provided herein may be cloned into a vector. Thus, the present invention also relates to a vector comprising the polynucleotide as described and provided herein. The term "vector" as used herein particularly refers to plasmids, cosmids, viruses, bacteriophages and other vectors commonly used in genetic engineering. In a preferred embodiment, these vectors are suitable for the transformation of cells, like fungal cells, cells of microorganisms such as yeast or prokaryotic cells. In a particularly preferred embodiment, such vectors are suitable for stable transformation of bacterial cells, for example to express the polynucleotides of the present invention.

Accordingly, in one aspect of the invention, the vector as provided is an expression vector. Generally, expression vectors have been widely described in the literature. As a rule, they may not only contain a selection marker gene and a replication-origin ensuring replication in the host selected, but also a promoter, and in most cases a termination signal for transcription. Between the promoter and the termination signal there is preferably at least one restriction site or a polylinker which enables the insertion of a nucleic acid sequence/molecule desired to be expressed.

It is to be understood that when the vector described and provided herein is generated by taking advantage of an expression vector known in the prior art that already comprises a promoter suitable to be employed in context of this invention, for example expression of a polynucleotide as described hereinabove, the nucleic acid construct is inserted into that vector in a manner the resulting vector comprises only one promoter suitable to be employed in context of this invention. The skilled person knows how such insertion can be put into practice. For example, the promoter can be excised either from the nucleic acid construct or from the expression vector prior to ligation.

Non-limiting examples for the vector into which a polynucleotide described and provided herein is cloned are adenoviral, adeno-associated viral (AAV), lentiviral, HIV-based lentiviral, or nonviral minicircle-vectors. Further examples of vectors suitable to comprise the polynucleotide of the present invention to form the vector described herein are known in the art and are, for example, other vectors for bacterial and eukaryotic expression systems.

Furthermore, in context of the present invention, the polynucleotides and/or the vector described and provided herein may be transduced, transformed or transfected or otherwise introduced into a host cell. Thus, the present invention also relates to a host cell comprising the polynucleotide and/or the vector as described and provided herein. For example, the host cell is a prokaryotic cell, for example, a bacterial cell. As a non-limiting example, the host cell may also be a mammalian cell. The host cell described herein is intended to be particularly useful for generating the peptides described and provided herein. Generally, the host cell described herein may be a prokaryotic or eukaryotic cell, comprising the polynucleotide or the vector described and provided herein or a cell derived from such a cell and containing the nucleic acid construct or the vector. In one embodiment, the host cell comprises, i.e. is genetically modified with the polynucleotide or the vector described and provided herein in such a way that it contains the polynucleotide integrated into the genome. For example, such host cells described herein may be bacterial, yeast, or fungus cells. In one particular aspect, the host cell may be capable to express or expresses a polynucleotide of the present invention. An overview of examples of different corresponding expression systems to be used for generating the host cell described herein is for instance contained in Methods in Enzymology 1.53 (1987), 385-516, in Bitter (Methods in Enzymology 153 (1987), 516-544), in Sawers (Applied Microbiology and Biotechnology 46 (1996), 1-9), Billman-Jacobe (Current Opinion in Biotechnology 7 (1996), 500-4), Hockney (Trends in Biotechnology 12 (1994), 456-463), and in Griffiths, (Methods in Molecular Biology 75 (1997), 427-440). The transformation or genetically engineering of the host cell with a polynucleotide or vector described and provided herein can be carried out by standard methods, as for instance described in Sambrook and Russell (2001), Molecular Cloning: A Laboratory Manual, CSH Press, Cold Spring Harbor, N.Y., USA; Methods in Yeast Genetics, A Laboratory Course Manual, Cold Spring Harbor Laboratory Press, 1990.

The present invention further relates to compositions comprising peptides, polynucleotides, vectors and/or host cells as described and provided herein. Such compositions may be administered to a subject in need of medical intervention in an amount of about 1 ng/kg body weight to about 100 mg/kg body weight. Such a subject may be a mammal, e.g., a human being who is in need to be treated or in which disorders associated with aberrant GTPase activity as described herein are to be prevented. As mentioned, in context of the present invention, examples for diseases or disorders associated with aberrant GTPase activity are diseases associated with a localized or systemic breakdown of epithelial or endothelial barrier functions. Particular diseases and disorders to be treated and/or prevented in this context are burns, acute lung injury (ALI), acute respiratory distress syndrome (ARDS), ventilator induced lung injury (VILI), systemic inflammatory response syndrome (SIRS), acute kidney injury (AKI), sepsis, multiorgan dysfunction syndrome (MODS), or edema. The composition described and provided herein may comprise the peptides of the present invention in an amount of about 1 µg/kg body weight to about 40 mg/kg body weight per day, or about 1 mg/kg body weight to about 30 mg/kg body weight, or about 1 mg/kg body weight to about 20 mg/kg body weight per day, or about 1 mg/kg body weight to about 15 mg/kg body weight per day, or about 1 mg/kg body weight to about 10 mg/kg body weight per day, or about 10 mg/kg body weight to about 15 mg/kg body weight per day.

In context of the present invention, the composition comprising peptides, polynucleotides, vectors and/or host cells as described and provided herein may further comprise a pharmaceutically acceptable carrier. Accordingly, the present invention also relates to a pharmaceutical composition comprising peptides, polynucleotides, vectors and/or host cells as described and provided herein and, optionally, further comprising a pharmaceutically acceptable carrier, excipient and/or diluent. Generally, examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose, i.e. about 1 µg/kg body weight to about 40 mg/kg body weight per day, or about 1 mg/kg body weight to about 30 mg/kg body weight, or about 1 mg/kg body weight to about 20 mg/kg body weight per day, or about 1 mg/kg body weight to about 15 mg/kg body weight per day, or about 1 mg/kg body weight to about 10 mg/kg body weight per day, or about 10 mg/kg body weight to about 15 mg/kg body weight per day. Administration of the (pharmaceutical) compositions may be effected or administered by different ways, e.g., parenterally (e.g., intravenously, subcutaneous, transdermally, intramuscularly or intraperitoneally), via inhalation (e.g., intrabronchially), as an erodible implant made of biodegradable polymers (e.g., polylactate or polyglycolate), enterally (e.g., pill, tablet (buccal, sublingual, orally, disintegrating, capsule, thin film, liquid solution or suspension), powder, solid crystals or liquid), rectally (e.g., suppository, enema), transdermally, topically, vaginally, epicutaneously, or intranasally. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. The (pharmaceutical) compositions comprising peptides, polynucleotides, vectors and/or host cells as described and provided herein may be administered locally or systemically. Administration of the peptides of the present invention will preferably be parenterally, e.g., intravenously or subcutaneously. The (pharmaceutical) compositions comprising peptides, polynucleotides, vectors and/or host cells as described and provided herein may also be administered directly to the target site, e.g., by biolistic delivery to an internal or external target site or by catheter to a site in an artery. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, also doses below or above of the exemplary ranges described hereinabove are envisioned, especially considering the aforementioned factors. The peptides of the present invention may also be used in combinations of two or more peptides provided herein. Accordingly, the compositions of the present invention may comprise two or more peptides provided herein, optionally also in combination with other compounds described and provided herein. Moreover, the peptides of the present invention may be used in co-therapy in conjunction with vasoactive agents such as nitric oxide, prostacyclin, exogenous surfactants, anticoagulants, agents targeting tissue factor activity, agents with the potential to improve alveolar fluid clearance such as $\beta_2$-agonists, agents inhibiting TNF actions, anti-IL-8 and anti-CD40L therapies (Curr Med Chem (2008), 15(19): 1911-1924), inhaled activated protein C (Crit Care (2010), 14(2): R70), immunosuppressants such as glucocorticosteroids or cyclosporine, antibiotics, HES solutions, colloids used for volume expansion (Emerg Med J (2003), 20: 306-315), or agents targeting pathologic imbalance of the renin-angiotensin system.

The skilled person knows that the effective amount of pharmaceutical compositions administered to an individual will, inter alia, depend on the nature of the compound. For example, if said compound is a peptide as described herein, the total pharmaceutically effective amount of pharmaceutical composition administered parenterally per dose may be in the range of about 1 µg/kg/day to 100 mg/kg/day of patient body weight, or 1 µg/kg body weight to about 40 mg/kg body weight per day, or about 1 mg/kg body weight to about 30 mg/kg body weight, or about 1 mg/kg body weight to about 20 mg/kg body weight per day, or about 1 mg/kg body weight to about 15 mg/kg body weight per day, or about 1 mg/kg body weight to about 10 mg/kg body weight per day, or about 10 mg/kg body weight to about 15 mg/kg body weight per day, although, as noted above, this will be subject to therapeutic discretion. However, this dose may be further decreased or increased subject to therapeutic discretion, in particular if concomitantly certain lipids are applied or if the peptide is subject to certain chemical modifications. The particular amounts may be determined by conventional tests which are well known to the person skilled in the art.

The pharmaceutical composition described and provided herein may be also suitably administered by sustained release systems. Suitable examples of sustained-release compositions include semi-permeable polymer matrices in the form of shaped articles, e.g., films, or microcapsules. Sustained-release matrices include polylactides (U.S. Pat. No. 3,773,919, EP-A1 58481), copolymers of L-glutamic acid and gamma-ethyl-L-glutamate (Biopolymers (1983), 22: 547-556), poly (2-hydroxyethyl methacrylate) (J Biomed Mater Res (1981), 15: 167-277; Langer, Chem Tech (1982), 12: 98-105), ethylene vinyl acetate (Langer, loc. cit.) or poly-D-(−)-3-hydroxybutyric acid (EP-A1 133988). Sustained release pharmaceutical compositions may also include liposomally entrapped compounds. Liposomes containing the pharmaceutical composition may be prepared by methods known in the art, such as described in DE 3218121; Proc Natl Acad Sci USA (1985), 82: 3688-3692; Proc Natl Acad Sci USA 77: 4030-4034 (1980); EP-A1 52322; EP-A1 36676; EP-A1 88046; EP-A1 143949; EP-A1 142641; Japanese Pat. Appl. 83-118008; U.S. Pat. Nos. 4,485,045 and 4,544,545; and EP-A1 102324.

In context of the present invention, the formulations described herein may be prepared by contacting the components of the pharmaceutical composition uniformly and intimately with liquid carriers or finely divided solid carriers or both. Then, if necessary, the product may be shaped into the desired formulation. The carrier may be a parenteral carrier, e.g., a solution that is isotonic with the blood of the recipient. Examples of such carrier vehicles include water, saline, Ringer's solution, and dextrose solution. Non-aqueous vehicles such as fixed oils and ethyl oleate may also be useful herein, as well as liposomes as described herein. The carrier may suitably contain minor amounts of additives such as substances that enhance isotonicity and chemical stability. Such materials are preferably non-toxic to recipients at the dosages and concentrations employed, and may include buffers such as phosphate, citrate, succinate, acetic acid, and other organic acids or their salts; antioxidants such as ascorbic acid; low molecular weight (less than about ten residues) (poly)peptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

In context of the present invention, the components of the pharmaceutical composition to be used for therapeutic administration are preferably sterile. Sterility may readily be accomplished by, e.g., filtration through sterile filtration membranes (e.g., 0.2 micron membranes). Therapeutic components of the pharmaceutical composition may be placed into a container having a sterile access port, for example, an intravenous solution bag or vial having a stopper pierceable by a hypodermic injection needle. The components of the pharmaceutical composition ordinarily may be stored in unit or multi-dose containers, for example, sealed ampoules or vials, as an aqueous solution or as a lyophilized formulation for reconstitution. As a non-limiting example of a lyophilized formulation, 10-ml vials may be filled with 5 ml of sterile-filtered 1% (w/v) aqueous solution, and the resulting may be is lyophilized. The infusion solution may be prepared by reconstituting the lyophilized compound(s) using bacteriostatic Water-for-Injection.

In context of the present invention, the peptides, polynucleotides, vectors, host cells, compositions and pharmaceutical compositions described and provided herein may be used in treating or preventing diseases or disorders associated with aberrant GTPase activity. Non-limiting examples for diseases and disorders associated with aberrant GTPase activity are diseases associated with a localized or systemic breakdown of epithelial or endothelial barrier functions. Particular diseases and disorders comprise burns, acute lung injury (ALI), acute respiratory distress syndrome (ARDS), ventilator induced lung injury (VILI), systemic inflammatory response syndrome (SIRS), acute kidney injury (AKI), sepsis, multiorgan dysfunction syndrome (MODS), or edema.

For example, the present invention relates to a peptide comprising or consisting of the sequence GRRPLGGISGG (SEQ ID NO: 3) for use in treating or preventing a disease or disorder selected from the group consisting of diseases associated with a localized or systemic breakdown of epithelial or endothelial barrier functions. Particular diseases and disorders to be treated and/or prevented by the means and methods provided herein comprise burns, acute lung injury (ALI), acute respiratory distress syndrome (ARDS), ventilator induced lung injury (VILI), systemic inflammatory response syndrome (SIRS), acute kidney injury (AKI), sepsis, multiorgan dysfunction syndrome (MODS), or edema.

The present invention further relates to a method of treating or preventing a disease or disorder associated with a localized or systemic breakdown of epithelial or endothelial barrier functions. In context with the present invention, particular diseases and disorders to be treated and/or prevented by the method provided herein or by the compounds provided herein comprise particularly burns, acute lung injury (ALI), acute respiratory distress syndrome (ARDS), ventilator induced lung injury (VILI), systemic inflammatory response syndrome (SIRS), acute kidney injury (AKI), sepsis, multiorgan dysfunction syndrome (MODS), or edema. Such methods particularly comprise the administration of an effective dose of (a) peptide(s), polynucleotide(s), vector(s(, host cell(s), composition(s) and/or pharmaceutical composition(s) described and provided herein to a subject. In one embodiment, the subject is human.

The Figures show:

FIG. 1: Ventilator-Induced Lung Injury (VILI)

Total cell counts, neutrophil counts, protein and IgM content served as surrogate parameter to assess barrier dysfunction. (* p>0.05 p>0.01; * p>0.001). Abbreviations are: LPS: LPS inhalation; LVt: low volume tide ventilation; HVt: high volume tide ventilation, sc: scrambled peptide GGGGGSRRIPL (SEQ ID NO: 38); XIB1-b: GRRPLGGISGG (SEQ ID NO: 3).

FIG. 1 compares effects of LPS challenge followed by LVt or HVt on total cell counts, neutrophil counts, total protein content and IgM content within broncheoalveolar lavages in animals treated with sc or XIB1-b. In all groups, XIB1-b reduces all parameters. Significance was obtained as indicated by asterices (*p<0.5, ***p<0.01).

The following examples illustrate the invention.

EXAMPLE 1

Peptides

For the following exemplary studies, peptides of the present invention with the amino acid sequence GRRPG- GASGG (SEQ ID NO: 39; called XIB1-a) and GRRPLG-GISGG (SEQ ID NO: 3; called XIB1-b) were used as active agent. For control purposes, a random peptide with the amino acid sequence GGGGGLSRRIP (SEQ ID NO: 40) or solvent control (0.9% NaCl) were used. These peptide as well as all other peptides claimed were synthesized by standard FMOC-Synthesis as described in the literature (e.g., solid phase peptide synthesis—"A practical approach" by E. Atherton, R. C. Sheppard, Oxford University press 1989) or by liquid phase synthesis where the peptides are assembled using a mixed strategy by BOC-chemistry and fragment condensation as described in the literature (E. Wünsch, "Synthese von Peptiden" in "Methoden der organischen Chemie" (Houben-Weyl), 15 Ausg. 4, Teil 1 und 2 Thieme, Stuttgart, 1974).

EXAMPLE 2

Inhibition of GEF-Activity

To measure the GEF-inhibitory effect, the following cell lines were used: Caco-2 (epithelial cells from adeno-carcinoma), ECV304 (epithelial cells from bladder carcinoma) and HpMec (endothelial cells, immortalized pulmonary micro-vascular cells). All cells were grown at standard conditions (37° C., 5% $CO_2$ and 95% relative humidity (rH)). Culture Medium used for Caco-2: DMEM+1 mM sodium pyruvate+20% FCS+1% Penicillin Streptomycin; for ECV 304: RPMI 1640+10% FCS+1% Penicillin Streptomycin; and for HpMec: IMDM+25 mM Hepes+10% Human Serum+1% Penicillin Streptomycin+1% L-Glutamine+ECGS/Heparin 2 ml. 4 h before the experiment, cells were starved by serum withdrawal. To induce GEF-activity, cells were stimulated with thrombin, lipopolysaccharide (LPS) or PMA for the indicated time in presence or absence of 50 µg/ml XIB1-a or XIB1-b. After stimulation, membrane fractions were prepared by using the commercial available "Compartemental Protein Extraction Kit" from Biochain institutes. Membrane fractions were prepared according to the manufacturer instructions. GEF-activity in membrane lysates was determined by using "RhoGEF Exchange Assay Biochem Kit" from Cytoskeleton Inc. according to manufacturer instructions. GEF-activity was measured as fluorescence at using the Fluoroskan Ascent FL 2.6 from Thermo Electron Corporation. The excitation Filter wavelength was set at 355 nm and the emission filter wavelength at 460 nm.

TABLE 1

Relative values compared to unstimulated control; (*) $p < 0.05$ compared to tests w/o XIB1-a or XIB1-b

|  | Mean | SD |
|---|---|---|
| ECV 304 Zellen | | |
| Control Peptide 1 min | 1 | 0.5 |
| Control Peptide 5 min | 1 | 0.5 |
| XIB1-a or XIB1-b 1 min | 1 | 0.4 |
| XIB1-a or XIB1-b 5 min | 1 | 0.3 |
| Thrombin 1 U/ml 1 min | 5 | 1.1 |
| Thrombin 1 U/ml 5 min | 3.4 | 0.9 |
| Thrombin 1 U/ml + XIB1-a or XIB1-b; 1 min | 2.5* | 1 |
| Thrombin 1 U/ml + XIB1 a or XIB1-b; 5 min | 1.5* | 0.2 |
| LPS 100 µg/ml, 1 min | 3.2 | 1.1 |
| LPS 100 µg/ml, 5 min | 3.2 | 1.1 |
| LPS 100 µg/ml + XIB1-a or XIB1-b, 1 min | 1.7* | 0.9 |
| LPS 100 µg/ml + XIB1a or XIB1-b, 5 min | 1.3* | 0.8 |

TABLE 1-continued

Relative values compared to unstimulated control; (*) $p < 0.05$ compared to tests w/o XIB1-a or XIB1-b

|  | Mean | SD |
|---|---|---|
| CaCo-2 | | |
| Control Peptide 1 min | 1 | 0.2 |
| Control Peptide 5 min | 1 | 0.3 |
| XIB1-a or XIB1-b 1 min | 1 | 0.5 |
| XIB1-a or XIB1.b 5 min | 1 | 0.5 |
| PMA 1 µg/ml 1 min | 2.5 | 0.5 |
| PMA 1 µg/ml 5 min | 1.8 | 0.8 |
| PMA 1 µg/ml + XIB1-a or XIB1-b; 1 min | 1.4* | 0.2 |
| PMA 1 µg/ml + XIB1a or XIB1-b; 5 min | 1.5 | 0.3 |
| HpMec | | |
| Control Peptide 1 min | 1 | 0.2 |
| Control Peptide 5 min | 1 | 0.2 |
| XIB1-a or XIB1-b 1 min | 1 | 0.3 |
| XIB1-a or XIB1-b 5 min | 1 | 0.5 |
| Thrombin 1 U/ml 1 min | 3.5 | 1.1 |
| Thrombin 1 U/ml 5 min | 3 | 0.6 |
| Thrombin 1 U/ml + XIB1-a or XIB1-b; 1 min | 1.8* | 0.4 |
| Thrombin 1 U/ml + XIB1-a or XIB1-b; 5 min | 2.1* | 0.6 |

As can be taken from Table 1, in ECV304 cells, thrombin and LPS stimulation resulted in an increase of GEF-activity compared to untreated control cells. ECV 304 cells stimulated with thrombin or LPS in the presence of XIB1-a or XIB1-b show a significant reduction of GEF-activity compared with treatment with thrombin or LPS alone.

In CaCo-2 cells, a 1 min PMA-stimulus resulted in an increase of GEF-activity by 2.5 fold. The magnitude of GEF-activation was significantly reduced when CaCo-2 cells were co-treated with PMA and XIB1-a or XIB1-b.

In HepMec cells, thrombin induced a 3.5-fold increase in GEF-activity after 1 min and a 3-fold increase after 5 min of stimulation. Co-treatment of cells with XIB1-b significantly reduced the magnitude of GEF-activity after 1 min and after 5 min. Treatment with XIB1-a or XIB1-b alone did not alter basic GEF-activity.

The results demonstrate that peptides of the present invention such as XIB1-a and XIB1-b reduce GEF-activity induced by different stimulating agents in epithelial and endothelial cells, but do not alter basic GEF-activity in unstimulated cells. This shows that the peptides of the present invention are useful in the treatment or prevention of diseases or disorders associated with aberrant GTPase activity. In this context, particular disorders and diseases may be diseases and disorders may be burns, acute lung injury (ALI), acute respiratory distress syndrome (ARDS), ventilator induced lung injury (VILI), systemic inflammatory response syndrome (SIRS), acute kidney injury (AKI), sepsis, multiorgan dysfunction syndrome (MODS), or edema.

EXAMPLE 3

Reduction of GTP-Associated RhoA

To measure the GTP-associated active RhoA, the following cell lines were used: Caco-2, ECV304 and HpMec. All cells were grown at standard conditions (37° C., 5% $CO_2$ and 95% rH). 4 h before the experiment, cells were starved by serum withdrawal. To induce GEF-activity, cells were stimulated with thrombin, LPS or PMA for the indicated time in presence or absence of 50 µg/ml XIB1-a or XIB1-b. After stimulation, membrane fractions were prepared by using the commercial available "Compartemental Protein Extraction Kit" from Biochain Institutes. Membrane fractions were prepared according to the manufacturer instructions. The membrane fraction was separated on 15% polyacrylamide gel according to standard procedures of gel electrophoresis. The gels were afterwards blotted on a nitrocellulose membrane according to standard procedures of western blotting. GTP-bound RhoA was detected using RhoA-GTP monoclonal antibody from NewEast Inc. in a dilution of 1:5000. Protein bands were analyzed with the Dolphin-1D Gel analysis system (Wealtec).

TABLE 2

Relative values compared to unstimulated control; (*) $p < 0.05$ compared to tests w/o XIB1-a or XIB1-b

|  | Mean | SD |
| --- | --- | --- |
| ECV 304 Zellen |  |  |
| Control Peptide 1 min | 1 | 0.1 |
| Control Peptide 5 min | 1 | 0.3 |
| XIB1-a or XIB1-b, 1 min | 1 | 0.5 |
| XIB1-1 or XIB1-b 5 min | 1 | 0.4 |
| Thrombin 1 U/ml 1 min | 4.3 | 1.1 |
| Thrombin 1 U/ml 5 min | 3.2 | 1.3 |
| Thrombin 1 U/ml + XIB1-a or XIB1-b; 1 min | 2.1* | 0.5 |
| Thrombin 1 U/ml + XIB1-a or XIB1-b; 5 min | 1.9* | 0.4 |
| LPS 100 µg/ml; 1 min | 2.7 | 1.1 |
| LPS 100 µg/ml; 5 min | 2.9 | 1.1 |
| LPS 100 µg/mL + XIB1-a or XIB1-b, 1 min | 1.6* | 1.6 |
| LPS 100 µg/ml + XIB1-a or XIB1-b, 5 min | 1.7* | 1 |
| CaCo-2 |  |  |
| Control Peptide 1 min | 1 | 0.3 |
| Control Peptide 5 min | 1 | 0.2 |
| XIB1-a or XIB1-b 1 min | 1 | 0.4 |
| XIB1-a or XIB1-b 5 min | 1 | 0.2 |
| PMA 1 µg/ml 1 min | 2.3 | 1.2 |
| PMA 1 µg/ml 5 min | 2.0 | 0.6 |
| PMA 1 µg/ml + XIB1-a or XIB1-b 1 min | 1.4* | 0.5 |
| PMA 1 µg/ml + XIB1-a or XIB1-b; 5 min | 1.3* | 0.1 |
| HpMec |  |  |
| Control Peptide 1 min | 1 | 0.3 |
| Control Peptide 5 min | 1 | 0.2 |
| XIB1-a or XIB1-b 1 min | 1 | 0.4 |
| XIB1-a or XIB1-b 5 min | 1 | 0.2 |
| Thrombin 1 U/ml 1 min | 3.8 | 1.1 |
| Thrombin 1 U/ml 5 min | 3.2 | 1.2 |
| Thrombin 1 U/ml + XIB1-a or XIB1-b 1 min | 2.1* | 0.3 |
| Thrombin 1 U/ml + XIB1-a or XIB1-b 5 min | 1.3* | 0.4 |

As can be taken from Table 2. in ECV304 cells, thrombin and LPS stimulation resulted in an increase of RhoA-activity compared to untreated control cells. ECV 304 cells stimulated with thrombin or LPS in the presence of XIB1-a or XIB1-b show a significant reduction in RhoA-activity compared with treatment with thrombin or LPS alone.

In CaCo-2 cells, PMA-stimulus resulted in a 2.3 fold increase of RhoA-activity after 1 min of stimulation and in a 2-fold increase of RhoA-activity after 5 mm of stimulation. The magnitude of RhoA-activation after 1 and after 5 min was significantly reduced when CaCo-2 cells were co-treated with PMA and XIB1-a or XIB1-b.

In HepMec cells, thrombin induced a 3.8-fold increase in RhoA-activity after 1 min and a 3.2-fold increase after 5 min of stimulation. Co-treatment of cells with XIB1-b significantly reduced the magnitude of RhoA-activity after 1 min and after 5 min. Treatment with XIB1-a or XIB1-b alone did not alter basic RhoA-activity.

These results demonstrate that peptides of the present invention such as XIB1-a or XIB1-b reduce RhoA-activity induced by different stimulating agents in epithelial and endothelial cells, but do not alter basic GEF-activity in unstimulated cells. RhoA-activity is controlled by GEF-activation as described above. The results demonstrate that XIB1-a and/or XIB1-b are decreasing RhoA-activity by inhibiting GEF-activity and, thus, are useful in the treatment and/or prevention of diseases or disorders associated with a localized or systemic breakdown of epithelial or endothelial barrier functions. Particularly, the peptides provided herein are useful in treating and/or preventing diseases and disorders such as burns, acute lung injury (ALI), acute respiratory distress syndrome (ARDS), ventilator induced lung injury (VILI), systemic inflammatory response syndrome (SIRS), acute kidney injury (AKI), sepsis, multiorgan dysfunction syndrome (MODS), or edema.

EXAMPLE 4

Phosphorylated Myosin Light Chain (MLC) and Actin Stress Fiber Formation

To measure MLC phosphorylation and actin stress fiber formation, the following cell lines were used: Caco-2, ECV304 and HpMec. All cells were grown at standard conditions (37° C., 5% $CO_2$ and 95% rH). Culture Medium used: for Caco-2: DMEM+1 mM sodium pyruvate+20% FCS+1% Penicillin Streptomycin; for ECV 304: RPMI 1640+10% FCS+1% Penicillin Streptomycin; and for HpMec: IMDM+25 mM Hepes+10% Human Serum+1% Penicillin Streptomycin+1% L-Glutamine+ECGS/Heparin 2 ml. 4 h before the experiment, cells were starved by serum withdrawal. To induce GEF-activity, cells were stimulated with thrombin, LPS or PMA for the indicated time in presence or absence of 50 µg/ml XIB1-a or XIB1-b. After stimulation, cells were fixed using 4% PFA. Phospho MLC was detected by using the "rabbit anti phosphor-myosin light chain antibody" from Chemicon in a concentration of 3 µl/ml in PBS (Gibco) supplemented with 0.1% Triton X-100. As detection antibody, the Alexa 448 tagged "anti Rabbit IgG Antibody" from Invitrogen was used in a concentration of 0.5 µl/ml in PBS (Gibco) supplemented with 0.1% Triton X-100. Aktin was detected using TRITC-labeled Phalloidin in a concentration of 0.5 µl/ml in PBS (Gibco) supplemented with 0.1% Triton. Stained cells were analyzed by using a Zeiss Laser Scan microscope. Evaluation of the cyto-skeletal activation was performed by 2 independent observers that were blinded to the conditions. Evaluation criteria were set as follows:

Actin: parallel actin bundles absent=0; distinct bundle formation=1; prominent parallel bundles=2; Phospho-MLC: present at cell poles=0; slight co-localization with actin bundles=1; prominent co-localization with actin bundles=2

TABLE 3

Relative values compared to unstimulated control; (*) p < 0.05 compared to tests w/o XIB1-a or XIB1-b; (*) p < 0.05 compared to tests w/o XIB1-a or XIB1-b

|  | Mean | SD |
|---|---|---|
| ECV 304 Zellen | | |
| Control Peptide 1 min | 0 | 0 |
| Control Peptide 5 min | 0 | 0 |
| Peptid XIB1-a or XIB1-b 1 min | 1 | 0.2 |
| Peptid XIB-a or XIB1-b 1 min | 0 | 0 |
| Thrombin 1 U/ml 1 min | 4 | 1.1 |
| Thrombin 1 U/ml 5 min | 4 | 1.4 |
| Thrombin 1 U/ml + XIB1-a or XIB1-b; 1 min | 1* | 0.3 |
| Thrombin 1 U/ml + XIB1-a or XIB1-b; 5 min | 1* | 1.1 |
| LPS 100 µg/ml 1 min | 3 | 1.2 |
| LPS 100 µg/ml 5 min | 3 | 1.3 |
| LPS 100 µg/ml + XIB1-a or XIB1-b, 1 min | 1* | 1.1 |
| LPS 100 µg/ml + XIB1-a or XIB1-b, 5 min | 1* | 1.2 |
| CaCo-2 | | |
| Control Peptide 1 min | 0 | 0 |
| Control Peptide 5 min | 0 | 0 |
| XIB1-a or XIB1-b 1 min | 0 | 0 |
| XIB1-a or XIB1-b 5 min | 0 | 0 |
| PMA 1 µg/ml 1 min | 3 | 0.3 |
| PMA 1 µg/ml 5 min | 3 | 1.2 |
| PMA 1 µg/ml + XIB1-a or XIB1-b; 1 min | 1* | 1.1 |
| PMA 1 µg/ml + XIB1-a or XIB1-b; 5 min | 2* | 1.3 |
| HpMec | | |
| Control Peptide; 1 min | 0 | 0 |
| Control Peptide; 5 min | 0 | 0 |
| XIB1-a or XIB1-b 1 min | 0 | 0 |
| XIB1-a or XIB1-b 5 min | 0 | 0 |
| Thrombin 1 U/ml 1 min | 4 | 2 |
| Thrombin 1 U/ml 5 min | 4 | 1.8 |
| Thrombin 1 U/ml + XIB1-a or XIB1-b; 1 min | 1* | 0.5 |
| Thrombin 1 U/ml + XIB1-a or XIB1-b; 5 min | 0.3* | 0.3 |

As can be taken from Table 3, in ECV304 cells, thrombin and LPS stimulation induced MLC phosphorylation and actin stressfiber formation. ECV 304 cells stimulated with thrombin or LPS in the presence of XIB1-a or XIB1-b show a significant reduction in MLC phosphorylation and actin stressfiber formation compared with treatment with thrombin or LPS alone.

In CaCo-2 cells, a PMA-stimulus induced an increase in MLC phosphorylation and actin stressfiber formation after 1 min and after 5 min of stimulation. The magnitude of Cytoskeletal activation after 1 and after 5 min was significantly reduced when CaCo-2 cells were co-treated with PMA and XIB1-a or XIB1-b.

In HepMec cells, thrombin induced an increase in MLC phosphorylation and actin stressfiber formation after 1 min and after 5 min of stimulation. Co-treatment of cells with XIB1-a or XIB1-b significantly reduced the magnitude of cytoskeletal activation after 1 min and after 5 min. Treatment with XIB1-a or XIB1-b alone did not alter basic cytoskeletal activity.

The results demonstrate that peptides of the present invention such as XIB1-a or XIB1-b reduce MLC phosphorylation and actin stressfiber formation induced by different stimulating agents in epithelial and endothelial cells. MLC phosphorylation and actin stressfiber formation is controlled RhoA-activity as described above. The results demonstrate that peptides of the present invention such as XIB1-a and/or XIB1-b are decreasing MLC phosphorylation and actin stressfiber by inhibiting GEF-activity and subsequent RhoA-activity and, thus, are useful in the treatment and/or prevention of diseases or disorders associated with a localized or systemic breakdown of epithelial or endothelial barrier functions. Particular diseases and disorders comprise burns, acute lung injury (ALI), acute respiratory distress syndrome (ARDS), ventilator induced lung injury (VILI), systemic inflammatory response syndrome (SIRS), acute kidney injury (AKI); sepsis, multiorgan dysfunction syndrome (MODS), or edema.

EXAMPLE 5

Endothelial and Epithelial Permeability

To measure permeability across endothelial and epithelial barriers, the following cell lines were used: Caco-2, (ECV304 and HpMec. All cells were grown to confluence at standard conditions on a transwell system (Costar) with a pore size of 4 µm. At the start of the experiment, growth media were withdrawn and substituted with Hank's buffered salt solution. The upper chamber was supplemented with 2 mg/ml FITC-labeled dextran (Sigma Aldrich). Cells were stimulated as indicated in Table 4. 30 min-samples from the lower chambers were collected and determined for fluorescence (Fluoroscan Ascent FL, Thermo Electron). 50 µg/ml XIB1-a and XIB1-b were added where indicated.

TABLE 4

Relative values compared to unstimulated control; (*) p < 0.05 compared to tests w/o XIB1-a or XIB1-b; (*) p < 0.05 compared to tests w/o XIB1-a or XIB1-b

|  | Mean | SD |
|---|---|---|
| ECV 304 Zellen | | |
| Control Peptide | 1 | 0.1 |
| XIB-1b | 1 | 0.3 |
| Thrombin 1 U/ml | 3 | 1.3 |
| Thrombin 1 U/ml XIB1-a or XIB1-b | 1.5* | 1 |
| LPS 100 µg/ml | 2.3 | 1 |
| LPS 100 µg/ml + XIB1 | 1.1* | 0.6 |
| CaCo-2 | | |
| Control Peptide | 1 | 0.3 |
| XIB1-a or XIB1-b | 1 | 0.3 |
| PMA 1 µg/ml 1 min | 2.5 | 1 |
| PMA 1 µg/ml + XIB1-a or XIB1-b | 1.4* | 0.6 |
| HpMec | | |
| Control Peptide | 1 | 0 |
| XIB1-a or XIB1-b | 1 | 0.5 |
| Thrombin 1 U/ml | 3.4 | 1.1 |
| Thrombin 1 U/ml + XIB1-a or XIB1-b | 1.8* | 1.3 |

As can be taken from Table 4, in ECV304 cells, thrombin and LPS stimulation increases barrier permeability. ECV 304 cells stimulated with thrombin or LPS in the presence of XIB1-a or XIB1-b show a significant reduction in barrier permeability compared with treatment with thrombin or LPS alone.

In CaCo-2 cells, PMA-stimulation induced an increase in barrier permeability. The barrier function was significantly improved when CaCo-2 cells were co-treated with PMA and XIB1-a or XIB1-b.

In HepMec cells, thrombin induced an increase in barrier permeability. Treatment of the cells with XIB1-a or XIB1-b significantly reduced the thrombin induced barrier permeability. Treatment with XIB1-a or XIB1-b or control peptide alone did not alter barrier function.

These results demonstrate that peptides of the present invention such as XIB1-a or XIB1-b reduce barrier permeability induced by different stimulating agents in epithelial and endothelial cells. Barrier permeability and barrier function is controlled by actin and myosin fibers. Activation of this cytoskeletal component results in cell contraction and cell rounding. Neighboring cells lose contact thereby increasing tissue permeability. Accordingly, The experiments demonstrate that peptides of the present invention such as XIB1-a and/or XIB1-b are decreasing barrier permeability induced by different agents in epithelial and endothelial cells and, thus, are useful in the treatment and/or prevention of diseases or disorders associated with a localized or systemic breakdown of epithelial or endothelial barrier functions. Particular diseases and disorders comprise burns, acute lung injury (ALI), acute respiratory distress syndrome (ARDS), ventilator induced lung injury (VILI), systemic inflammatory response syndrome (SIRS), acute kidney injury (AKI), sepsis, multiorgan dysfunction syndrome (MODS), or edema.

EXAMPLE 6

LPS Induced Lung Injury

Male C57Bl/6 Mice (Charles River, Germany) were kept at the animal facility of the Medical University of Vienna, feed with standard diet and water was provided ad libitum. All interventions were performed according to the guide lines of AAALAC (Association for Assessment and Accreditation of Laboratory Animal Care). All experiment were approved by the Ethic committee of the Medical University of Vienna. Mice were anesthetized with isoflouran and treated with 100 ng of LPS (*E. coli* O55:B5, Sigma Aldrich) intranasally. XIB1-a or XIB1-b was applied either intra-peritoneally (2×2 mg/kg) or via inhalation (2×4 mg/kg), first application was performed concomitantly with LPS administration, the second application was performed 1 h after the LPS inhalation.

Bronchioalveolar Lavage

After 6 h, mice were anesthetized with Ketamine (Pfizer, Vienna, Austria) and sacrificed by bleeding out the vena cava inferior. The trachea was exposed through a midline incision and canulated with a sterile 20-gauge catheter (BD Venflon™, Becton Dickinson Infusion Therapy, Helsingborg, Sweden). Bilateral broncho-alveolar lavage fluid (BALF) was gained by instilling two 0.5 ml aliquots of sterile saline. Approximately 0.9-1 ml BALF was retrieved per mouse. Total cell numbers were counted from each sample using a hemo-cytometer (Türck chamber), BALF differential cell counts were done on cytospin preparations stained with Giemsa. For protein measurements, BALF was diluted 1:2 in buffer containing 300 mM NaCl, 30 mM Tris, 2 mM $MgCl_2$, 2 mM $CaCl_2$, and Pepstatin A, Leupeptin and Aprotinin (all 20 ng/ml; pH 7.4). Protein levels in BALF were measured using the BCA protein kit according to the manufacturer's instructions (Pierce, Rockford, Ill.).

TABLE 5

Neutrophil counts and albumine content of the bronchio alveolar lavages serves as surrogate parameter for barrier dysfunction

| LPS + NaCl | LPS + Control-peptide | LPS + XIB1-b |
|---|---|---| n = 20 per experimental group, intraperitoneal application of XIB1-b
Values represent counts of neutrophils/ml (× $10^3$) in the BALF
(mean +/ SD) 6 h after LPS administration. The difference between XIB1-b and controls is significant (p < 0.05)

| 85 +/− 29 | 88 +/− 33 | 25 +/− 22 | n = 20 per experimental group, intraperitoneal application of XIB1-a or XIB1-b

TABLE 5-continued

Neutrophil counts and albumine content of the bronchio alveolar lavages serves as surrogate parameter for barrier dysfunction The values represent the albumine content of BALFs (μg/ml; mean +/ SD) 6 h after LPS administration. The difference between XIB1-b and controls is significant (p < 0.05)

| 220 +/− 15 | 212-10 | 120 +/− 12 |
|---|---|---|
| LPS + NaCl | LPS + Control-peptid | LPS plus XIB1-b | n = 20 per experimental group, intratracheal application of XIB1-b
Values represent counts of neutrophils/ml (× $10^3$) in the BALF
(mean +/ SD) 6 h after LPS administration. The difference between XIB1-b and controls is significant (p < 0.05)

| 80 +/− 28 | 90 +/− 30 | 28 +/− 23 | n = 20 per experimental group, intratracheal application of XIB1-a or XIB1-b
The values represent the albumine content of BALFs (μg/ml; mean +/ SD) 6 h after LPS administration. The difference between XIB1-b and controls is significant (p < 0.05)

| 244 +/− 28 | 237 +/− 32 | 98 +/− 20 |

As can be taken from Table 5, intranasal treatment of mice with LPS induced barriers dysfunction in the lung conveyed by increased neurophil influx and albumin accumulation in the bronchio-alveolar space. Treatment of mice with XIB1-b significantly improves barrier function, the mice showed less neutrophils and decrease of albumin in the BALF. The beneficial effect of XIB1-a or XIB1-b was equal in animal groups treated intraperitoneally and intratracheally.

Treatment of mice with control peptide did not alter the neutrophil counts and the albumin content of the BALF.

The LPS inhalation model is an accepted animal model to mimic ALI/ARDS as it resembles the human disease in regard to permeability changes in endothelial and epithelial cells and subsequent neutrophil and albumin accumulation in the bronchio alveolar space (Lung Cell Mol Physiol (2008), 295: L379-L399). The beneficial effect of XIB1-a or XIB1-b in the LPS-inhalation model demonstrates the usefulness of the peptides of the present invention to treat and/or prevent of diseases or disorders associated with a localized or systemic breakdown of epithelial or endothelial barrier functions. Specifically, the peptides of the present invention are useful in treating and/or preventing diseases and disorders such as, e.g., acute lung injury (ALI) or acute respiratory distress syndrome (ARDS).

Comparison XIB1-b with Bβ15-42

In addition, the same set-up as described above was used for comparing the impact of XIB1-b compared to Bβ15-42 (PLoS ONE (2009), 4(4): e5391), a peptide derived from fibrin having the sequence GHRPLDKKKREEAPSLRPAPPPISGGGYR (SEQ ID NO: 41). Bβ15-42 was added in the same manner as XIB1-b. Again, protein content and cell count of BALF was measured.

TABLE 6

| LPS + NaCl | LPS + Control-peptide | LPS + XIB1-b | LPS + Bβ15-42 |
|---|---|---|---| n = 20 per experimental group, intraperitoneal application of XIB1-b or Bβ15-42
Values represent counts of neutrophils/ml (× $10^3$) in the BALF
(mean +/ SD) 6 h after LPS administration. The difference between XIB1-b and controls is significant (p < 0.05)

| 89 +/− 29 | 91 +/− 33 | 27 +/− 26 | 33 +/− 22 | n = 20 per experimental group, intraperitoneal application of XIB1-b or Bβ15-42

TABLE 6-continued

| LPS + NaCl | LPS + Control-peptide | LPS + XIB1-b | LPS + Bβ15-42 |
|---|---|---|---|
| The values represent the albumine content of BALFs (µg/ml; mean +/ SD) 6 h after LPS administration. The difference between XIB1-b and controls as well as between XIB1-b and Bβ15-42 is significant ($p < 0.05$) | | | |
| 255 +/− 25 | 275-30 | 110 +/− 15 | 160 +/− 20 |
| n = 20 per experimental group, intratracheal plus intraperitoneal application of XIB1-b or Bβ15-42 Values represent counts of neutrophils/ml (× $10^3$) in the BALF (mean +/ SD) 6 h after LPS administration. The difference between XIB1-b and controls as well as between XIB1-b and Bβ15-42 is significant ($p < 0.05$) | | | |
| 88 +/− 24 | 94 +/− 30 | 15 +/− 15 | 35 +/− 10 |
| n = 20 per experimental group, intraperitoneal application of XIB1-b or Bβ15-42 The values represent the albumine content of BALFs (µg/ml; mean +/ SD) 6 h after LPS administration. The difference between XIB1-b and controls as well as between XIB1-b and Bβ15-42 is significant ($p < 0.05$) | | | |
| 279 +/− 34 | 250 +/− 25 | 80-12 | 152 +/− 35 |

Using the LPS-inhalation model, the effects of XIB1-b and Bβ15-42 on neutophil influx and albumin accumulation in the BALF were compared. Intraperitoneal treatment of mice with XIB1-b or Bβ15-42 reduced neutrophil infiltration in the BALF in a comparable range. Yet, as surprisingly found herein, XIB1-b was significantly more effective in reducing albumin content of the BALF as Bβ15-42. This clearly shows that XIB1-b is more efficient in treating and preventing diseases or disorders associated with a localized or systemic breakdown of epithelial or endothelial barrier functions as described herein. Particular diseases and disorders comprise burns, acute lung injury (ALI), acute respiratory distress syndrome (ARDS), ventilator induced lung injury (VILI), systemic inflammatory response syndrome (SIRS), acute kidney injury (AKI), sepsis, multiorgan dysfunction syndrome (MODS), or edema.

EXAMPLE 7

Ventilator-Induced Lung Injury (VILI)

Experiments were performed with healthy C57BL/6 (aged 8-10 weeks, with weights ranging from 19-25 g). All interventions were performed according to the guide lines of AAALAC. All experiment were approved by the Ethic committee of the University of Amsterdam.
Pre-Challenge with LPS.
Mice were challenged with LPS (dosage: 50 µg per mouse) (or saline), via intranasal injection 2 h before initiation of mechanical ventilation, to induce lung injury.
Administration of XIB1-b or Random Peptide.
XIB1-1b (or random peptide) was administered i.v. 10 min before start of mechanical ventilation (dosage: 4 mg/kg loading dose, followed administration i.v. injections 1 mg/kg/h.
Instrumentation and Anesthesia During Mechanical Ventilation.
Throughout the experiments rectal temperature was maintained between 36.5-37.5° C. using a warming path. Anesthesia was achieved with intra-peritoneal injection of a mix of ketamine, medetomidine, and atropine.
Mechanical Ventilation Strategies.
A Y-tube connector with 1.0 mm outer diameter and 0.6 mm inner diameter was surgically inserted into the trachea under general anesthesia. Mice were placed in a supine position and connected to a ventilator. Mice were pressure-controlled ventilated with either an inspiratory pressure of 10 cm $H_2O$ (resulting in $V_T$~7.5 mL/kg; low $V_T$, $LV_T$) or an inspiratory pressure of 18 cm $H_2O$ (resulting in $V_T$~15 mL/kg; high $V_T$, $HV_T$). Positive end-expiratory pressure (PEEP) is set at 2 cm $H_2O$ with both MV-strategies. The fraction of inspired oxygen was kept at 0.5 throughout the experiment. The inspiration to expiration ratio was kept at 1:1 throughout the experiment.
Fluid Support Strategies
Mice received intra-peritoneal boluses of normal saline 1 hour before start of MV, followed by boluses of normal saline via an intra-peritoneal catheter every 30 min.
Hemodynamic and Ventilatory Monitoring
Systolic blood pressure and heart rate were non-invasively monitored throughout the complete experiment. $V_T$ was checked hourly with a pneumotach system.
Measurements
BALF was obtained by instilling 3 times 0.5 mL aliquots of saline by a 22-gauge Abbocath-T catheter (Abbott, Sligo, Ireland) into the trachea. Approximately, 1.0 mL of BALF was retrieved per mouse and cell counts were determined using a hemacytometer (Beckman Coulter, Fullerton, Calif.). Subsequently, differential counts were done on cytospin preparations stained with a modified Giemsa stain, Diff-Quick (Dade Behring AG, Düdingen, Switzerland). Supernatant was stored at −80° C.
Assays
Total protein levels in BALF are determined using a Bradford Protein Assay Kit (OZ Biosciences, Marseille, France) according to manufacturers' instructions with bovine serum albumin as standard. Mouse IgM was determined by ELISA by using anti-Mouse IgM sensitized 96-strip micro-well plates according to manufacturers' instructions (IMMUNO-TEK kit from ZeptoMetrix).
As a result, it was shown that XIB1-b reduces lung inflammation which correlates with less lung damage and reduces pulmonary edema; cf. FIG. 1.
In this experiment, lung injury was induced by a pre-exposure of mice to LPS followed by mechanical ventilation with high or low tidal volume. Mice were either treated with XIB1-b or scrambled peptide. Treatment of mice with XIB1-b resulted in significant decrease of total cell count, neutrophil count, total protein content and IgM content in the BALF in the most aggressive experimental protocol (LPS-HTV). No improvement was observed by using scrambled peptide. Using the modest experimental protocol, XIB1-b (LPS+LTV) significantly reduced total cell counts and neutrophil counts in the BALF compared to scrambled peptide. The modest treatment protocol did not cause a pronounced increase in total protein conten and IgM content, thus no effect of XIB1-b could be observed.
The present animal model resembles the clinical situation of patients that develop ALI/ARDS as a sequel of pneumonia. The positive results obtained with XIB1-b demonstrate the suitability of the peptides of the present invention for treating or preventing diseases or disorders associated with a localized or systemic breakdown of epithelial or endothelial barrier functions. Particular diseases and disorders comprise burns, acute lung injury (ALI), acute respiratory distress syndrome (ARDS), ventilator induced lung injury (VILI), systemic inflammatory response syndrome (SIRS), acute kidney injury (AKI), sepsis, multiorgan dysfunction syndrome (MODS), or edema.

The invention claimed is:

1. A peptide with an amino acid sequence consisting of:

$$GX_1RPX_2X_3X_4X_5GGX_6 \quad \text{(SEQ ID NO: 1)}$$

Wherein
- $X_1$ is R;
- $X_2$ is either omitted or an amino acid selected from the group consisting of L and V;
- $X_3$ is either omitted or an amino acid sequence consisting of 1 to 5 amino acids;
- $X_4$ is either omitted or an amino acid sequence consisting of GG;
- $X_5$ is IS; and
- $X_6$ is either omitted or an amino acid sequence consisting of 1 to 5 amino acids.

2. Peptide of claim 1, further comprising $X_7$ at the C-terminus of the sequence, wherein $X_7$ is a moiety selected from the group consisting of NH$_2$, albumin, polyethyleneglycol, dextrane, ferritine, hydroxyethyl-starch and Fc-moiety of an antibody.

3. The peptide of claim 1, wherein $X_2$ is L or V.

4. The peptide of claim 3, wherein $X_2$ is L.

5. The peptide of claim 1, wherein $X_3$ is PPP.

6. The peptide of claim 1, wherein $X_4$ is GG.

7. The peptide of claim 1, wherein $X_6$ is omitted.

8. The peptide of claim 1, wherein $X_2$ is L, $X_3$ is omitted and X6 is omitted, or wherein $X_2$ is V, $X_3$ is omitted and $X_6$ is omitted.

9. The peptide of claim 1, wherein the amino acid sequence consist of:

GRRPLGGISGG; (SEQ ID NO: 3)

GRRPVGGISGG; (SEQ ID NO: 6)

GRRPLISGG; (SEQ ID NO: 4)

GRRPVISGG; (SEQ ID NO: 7)

GRRPLPPPISGG; (SEQ ID NO: 8)
and

GRRPVPPPISGG. (SEQ ID NO: 9)

10. A pharmaceutical composition comprising the peptide of claim 1 and a pharmaceutically acceptable carrier and/or diluent.

11. The peptide of claim 1, wherein the peptide is synthetic.

12. The peptide of claim 9, wherein the peptide is synthetic.

13. A method of treating a disease or disorder selected from the group consisting of acute lung injury (ALI), acute kidney injury (AKI), acute respiratory distress syndrome (ARDS), ventilator induced lung injury (VILI), systemic inflammatory response syndrome (SIRS), sepsis, burns and multiorgan dysfunction syndrome (MODS) by administering an effective dose of the pharmaceutical composition of claim 10 to a subject.

14. The method of claim 13, wherein the route of administration is parenterally or orally.

* * * * *